United States Patent
Schmitt et al.

(10) Patent No.: US 10,364,220 B2
(45) Date of Patent: Jul. 30, 2019

(54) SYNTHESIS OF SUCCINIMIDES AND QUATERNARY AMMONIUM IONS FOR USE IN MAKING MOLECULAR SIEVES

(71) Applicant: ExxonMobil Chemical Patents Inc., Baytown, TX (US)

(72) Inventors: Kirk D. Schmitt, Pennington, NJ (US); Stephen Zushma, Clinton, NJ (US); Allen W. Burton, Stewartsville, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/020,280

(22) Filed: Jun. 27, 2018

(65) Prior Publication Data

US 2018/0305309 A1    Oct. 25, 2018

Related U.S. Application Data

(62) Division of application No. 14/651,918, filed as application No. PCT/US2013/076198 on Dec. 18, 2013, now Pat. No. 10,035,762.

(60) Provisional application No. 61/740,932, filed on Dec. 21, 2012.

(30) Foreign Application Priority Data

Feb. 19, 2013  (EP) .................................. 13155734

(51) Int. Cl.
| | | |
|---|---|---|
| *A61K 31/4025* | (2006.01) | |
| *A61K 31/40* | (2006.01) | |
| *C07D 207/06* | (2006.01) | |
| *C07D 403/06* | (2006.01) | |
| *B01J 20/18* | (2006.01) | |
| *B01J 29/06* | (2006.01) | |
| *C01B 39/02* | (2006.01) | |
| *C01B 39/42* | (2006.01) | |
| *C07D 207/408* | (2006.01) | |
| *C01B 39/36* | (2006.01) | |
| *B01J 29/85* | (2006.01) | |
| *B01J 29/70* | (2006.01) | |
| *B01J 29/40* | (2006.01) | |
| *C07D 207/40* | (2006.01) | |
| *C07D 207/48* | (2006.01) | |
| *C01B 39/04* | (2006.01) | |
| *C01B 39/48* | (2006.01) | |
| *C01B 39/54* | (2006.01) | |

(52) U.S. Cl.
CPC ............ *C07D 207/06* (2013.01); *B01J 20/18* (2013.01); *B01J 29/40* (2013.01); *B01J 29/70* (2013.01); *B01J 29/7023* (2013.01); *B01J 29/7034* (2013.01); *B01J 29/85* (2013.01); *C01B 39/04* (2013.01); *C01B 39/365* (2013.01); *C01B 39/42* (2013.01); *C01B 39/48* (2013.01); *C01B 39/54* (2013.01); *C07D 207/40* (2013.01); *C07D 207/408* (2013.01); *C07D 207/48* (2013.01); *C07D 403/06* (2013.01)

(58) Field of Classification Search
CPC .. A61K 31/4025; A61K 31/40; C07D 207/06; C07D 403/06; B01J 20/18; B01J 29/06; C01B 39/02; C01B 39/42
USPC .................. 514/429, 422, 408; 548/579, 524
See application file for complete search history.

(56) References Cited

FOREIGN PATENT DOCUMENTS

WO    WO-2010099441 A2 *   9/2010   ........... C01B 37/005

* cited by examiner

*Primary Examiner* — Matthew P Coughlin
*Assistant Examiner* — Sagar Patel
(74) *Attorney, Agent, or Firm* — Darryl M. Tyus

(57) ABSTRACT

The present invention relates to the synthesis of succinimides, in particular to a method for the synthesis of a succinimide compound, comprising the step of reacting an alkyne, with carbon monoxide and ammonia or an amine, in the presence of an iron catalyst, wherein the reaction is carried out in an amine liquid phase and/or in the absence of an ether solvent. The succinimides may be reduced to quaternary ammonium cations which may be used as structure directing agents in the synthesis of molecular sieves.

9 Claims, No Drawings

US 10,364,220 B2

SYNTHESIS OF SUCCINIMIDES AND QUATERNARY AMMONIUM IONS FOR USE IN MAKING MOLECULAR SIEVES

CROSS REFERENCE TO RELATED APPLICATIONS

This application is a divisional application of U.S. application Ser. No. 14/651,918 filed 12 Jun. 2015, now allowed, which is a National Stage Application of International Application No. PCT/US2013/076198, filed 18 Dec. 2013, and claims the benefits of and the priorities to U.S. Ser. No. 61/740,932, filed 21 Dec. 2012, and EP Application No. 13155734.0, filed 19 Feb. 2013, which are hereby incorporated by reference in their entireties.

FIELD OF THE INVENTION

The present invention relates to the synthesis of succinimides, in particular to methods for the synthesis of succinimides from alkynes, carbon monoxide and amines in the presence of an iron catalyst. The present invention also relates to quaternary ammonium ions produced by the reduction of succinimides and to methods of synthesizing molecular sieves in which the quaternary ammonium ions are used as structure directing agents.

BACKGROUND

Succinimides are both useful as drug and chemical precursors and are useful in the synthesis of molecular sieves, including zeolite catalysts. Succinimides may be readily reduced to amines and then converted to quaternary ammonium ions. Quaternary ammonium ions are typically used as the structure directing agents in zeolite catalysts. For example, zeolite MCM-68 may be made from quaternary ammonium ions as is described in U.S. Pat. No. 6,049,018. Other known zeolites that are typically produced using quaternary ammonium ions include SSZ-13, SSZ-15, SSZ-24, SSZ-31, and SSZ-37 as described in U.S. Pat. Nos. 5,281,407 and 5,641,393. It is important to discover new succinimides and more efficient methods of synthesis of succinimides to facilitate the discovery of new zeolites and the preparation of known zeolites.

Known processes for the preparation of succinimides include cyclisation of diols with amines, as described in WO 2012/002913 and by Zhang, J. et al., *Angew. Chem. Int. Ed.* 2010, 49, 6391-6395; and the reaction of succinic anhydrides with amines, as described in U.S. Pat. Nos. 5,554,768 and 4,847,069. Succinimides may also be produced from alkynes using iron carbonyl species, amines and copper chloride oxidation catalysts as described by Periasamy, M. et al. in *J. Organomet. Chem.* 2002, 649, 209-213.

A further process recently reported by Driller, K. M. et al., *Angew. Chem. Int. Ed.* 2009, 48, 6041-6044 and *Chem. Eur. J.* 2010, 16, 9606-9615 involves the reaction of an alkyne, carbon monoxide, and an amine in the presence of an iron catalyst. That process is an extremely efficient method to synthesize succinimides and has the advantage that the iron catalyst is innocuous and the advantage of being extremely flexible, allowing a wide range of substituent groups to be incorporated into the succinimides enabling the preparation of complex succinimide molecules, and hence complex quaternary ammonium ions for incorporation into zeolite catalysts, from small, readily available molecules. However, the process described by Driller, K. M. et al. (ibid.) is carried out in relatively high dilution in an ether solvent under an inert, i.e., air and water free, conditions and requires a large excess of amine over alkyne. For example, in the reaction of 270 mmol 3-hexyne (22 g) and cyclohexylamine to form 1-cyclohexyl-3,4-diethylpyrrolidine-2,5-dione, the method of Driller, K. M. et al. (ibid.) required air free, dry conditions, a 13 fold excess of amine, needed a 2 L reactor and produced a 56% yield of product. Thus, there remains a need for an improved method of synthesizing succinimides from alkyne starting materials, in particular, a need for an improved iron-catalyzed carbonylation process to prepare succinimides from alkynes and amines. There also remains a need for new structure directing agents for use in the synthesis of molecular sieves.

Molecular sieve materials, both natural and synthetic, have been demonstrated in the past to be useful as adsorbents and to have catalytic properties for various types of hydrocarbon conversion reactions. Certain molecular sieves, such as zeolites, AlPOs, and mesoporous materials, are ordered, porous crystalline materials having a definite crystalline structure as determined by X-ray diffraction (XRD). Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Such molecular sieves, both natural and synthetic, include a wide variety of positive ion-containing crystalline silicates. These silicates can be described as rigid three-dimensional frameworks of $SiO_4$ and Periodic Table Group 13 element oxide (e.g., $AlO_4$). The tetrahedra are cross-linked by the sharing of oxygen atoms with the electrovalence of the tetrahedra containing the Group 13 element (e.g., aluminum or boron) being balanced by the inclusion in the crystal of a cation, for example, a proton, an alkali metal or an alkaline earth metal cation. This can be expressed wherein the ratio of the Group 13 element (e.g., aluminum or boron) to the number of various cations, such as $H^+$, $Ca^{2+}/2$, $Sr^{2+}/2$, $Na^+$, $K^+$, or $Li^+$, is equal to unity.

Molecular sieves that find application in catalysis include any of the naturally occurring or synthetic crystalline molecular sieves. Examples of these molecular sieves include large pore zeolites, intermediate pore size zeolites, and small pore zeolites. These zeolites and their isotypes are described in "Atlas of Zeolite Framework Types", eds. Ch. Baerlocher, L. B. McCusker, D. H. Olson, Elsevier, Sixth Revised Edition, 2007, which is hereby incorporated by reference. A large pore zeolite generally has a pore size of at least about 6.5 to 7 Å and includes LTL, MAZ, FAU, OFF, *BEA, and MOR framework type zeolites (IUPAC Commission of Zeolite Nomenclature). Examples of large pore zeolites include mazzite, offretite, zeolite L, zeolite Y, zeolite X, omega, and beta. An intermediate pore size zeolite generally has a pore size from about 4.5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, ZSM-57, MCM-22, silicalite 1, and silicalite 2. A small pore size zeolite has a pore size from about 3 Å to less than about 5.0 Å and includes, for example, AEI, CHA, ERI, KFI, LEV, SOD, and LTA framework type zeolites (IUPAC Commission of Zeolite Nomenclature). Examples of small pore zeolites include ZK-4, SAPO-34, SAPO-35, ZK-14, SAPO-42, ZK-21, ZK-22, ZK-5, ZK-20, zeolite A, chabazite, zeolite T, and ALPO-17.

Synthesis of molecular sieve materials typically involves the preparation of a synthesis mixture which comprises sources of all the elements present in the molecular sieve often with a source of hydroxide ion to adjust the pH. In many cases a structure directing agent is also present. Structure directing agents are compounds which are believed to promote the formation of molecular sieves and which are thought to act as templates around which certain molecular sieve structures can form and which thereby promote the formation of the desired molecular sieve. Various compounds have been used as structure directing agents, including various types of quaternary ammonium cations. However, there remains a need for new structure directing agents which offer the possibility of improving the synthesis of known molecular sieves or of allowing the synthesis of new molecular sieve materials.

The synthesis of molecular sieves is a complicated process. There are a number of variables that need to be controlled in order to optimize the synthesis in terms of purity, yield and quality of the molecular sieve produced. A particularly important variable is the choice of synthesis template (structure directing agent), which usually determines which framework type is obtained from the synthesis. This is mentioned, for example, in U.S. Pat. No. 4,310,440 (Wilson et al.), which teaches that "not all templating agents suitably employed in the preparation of certain species are suitable for the preparation of all members of the generic class." It is also well known that the same template may induce the formation of different framework types. Accordingly, there is a need for new templates and new ways of making molecular sieves.

SUMMARY OF THE INVENTION

The present invention provides a method for the synthesis of a succinimide compound, comprising the step of reacting an alkyne, carbon monoxide and an amine reagent, which is either ammonia or a primary amine, in the presence of an iron catalyst, under conditions in which a liquid phase is present, wherein at least 50% by volume of the liquid phase is amines. The present invention further provides a method for the synthesis of a succinimide compound, comprising the step of reacting an alkyne, with carbon monoxide and an amine reagent, which is either ammonia or a primary amine, in the presence of an iron catalyst, under conditions in which a liquid phase is present, wherein the reaction is carried out either in the absence of an ether solvent, or, if ether solvents are present, the molar ratio of ether solvents to amines is no more than 1:1. The reaction may, for example, be carried out as a solvent-free reaction in which the bulk of the liquid phase is amine reagents, such as an excess of primary amine, or in a solvent system, such as a tertiary amine solvent, which does not include a substantial amount of ether solvent. Preferably, at least 50% by volume of the liquid phase is amines and the reaction of the present invention is carried out either in the absence of an ether solvent, or, if ether solvents are present, the molar ratio of ether solvents to amines is no more than 1:1.

The present invention provides, in a further aspect, a process for producing a molecular sieve, the process comprising the steps of: i) preparing a synthesis mixture capable of forming a molecular sieve, said synthesis mixture comprising a source selected from a source of a tetravalent element Y, a source of a trivalent element X, or a mixture of a source of tetravalent element Y and a source of trivalent element X, and, optionally, a source of pentavalent element Z, optionally a source of hydroxide ions, optionally, a source of halide ions W and, optionally, a source of alkali metal ions $M^+$, the synthesis mixture further comprising a structure directing agent Q comprising a cation comprising a pyrrolidinium group in which the ring nitrogen is a quaternary ammonium nitrogen and in which at least one, and preferably both, of the 3- and the 4-positions on the pyrrolidinium ring is substituted with a substituent group other than hydrogen; ii) heating said synthesis mixture under crystallization conditions for a time of from about 1 to about 100 days to form crystals of said molecular sieve; and iii) recovering said crystals of the molecular sieve from the synthesis mixture.

The molecular sieve may be an aluminosilicate or a borosilicate. The molecular sieve may be an aluminophosphate or a silicoaluminophosphate.

In a further aspect, the invention provides a crystalline molecular sieve made by the process of the invention. In its "as-synthesized" form the molecular sieve includes the structure directing agent within its pores.

The invention also provides in further aspects the use of an active form of the crystalline molecular sieve as a sorbent or catalyst, and a process for converting a feed stock comprising an organic compound to a conversion product which comprises contacting said feedstock at organic compound conversion conditions with a catalyst comprising an active form of the molecular sieve.

DETAILED DESCRIPTION OF THE INVENTION

The Synthesis of Succinimides

The present inventors have found that, by eliminating the ether solvent the reaction may be carried out with either a reduced excess of amine, compared to the method of Driller, K. M. et al. (ibid.), or with stoichiometric amine and an unreactive tertiary amine, for example triethylamine, as solvent. The bulk liquid in which the reaction is carried out may, for example, be amines. For example, the bulk liquid may be an excess of primary amine reagent or a mixture of primary amine reagent and tertiary amine solvent. The method of the present invention has been found to enable the reaction to be carried out more efficiently with increased yields being obtained, lower quantities of starting materials being required and/or smaller size reactor being used to generate the same quantity of product. For example, using the method of the present invention, 270 mmol of 3-hexyne has been converted to 1-cyclohexyl-3,4-diethylpyrrolidine-2,5-dione in 91% yield in a 0.3 L reactor with no need to use dry reagents or use inert gas conditions. The nearly 7-fold reduction in reactor size compared with that used in the method of Driller, K. M. et al. (ibid.) results in a significant reduction in capital expense and a dramatic increase in safety because of the large reduction in the need for toxic carbon monoxide.

The reaction of the present invention is carried out under conditions in which a liquid phase is present, for example, as a liquid or mixed liquid-gas phase reaction. Typically, the reaction will be a mixed phase reaction. A gaseous phase is typically present in the reactor, for example, a gaseous phase that is rich in carbon monoxide. It is well known and well within the capability of the skilled person to carry out reactions under conditions in which a liquid phase is present.

The majority or bulk of the liquid phase is amines, including any primary amine reagents present and optional tertiary amine solvents. Typically, at least 60% by volume, such as at least 65% by volume, especially at least 70% by volume, for example at least 75% by volume of the liquid phase is amines. In some embodiments, at least 80% by volume of the liquid phase is amines. The remainder of the liquid phase is typically made of the other reagents, including the alkyne. The iron catalyst is typically present in the liquid phase, for example, in suspension or solution. Advantageously, solvents other than tertiary amines, especially ether solvents, are absent from the liquid phase. If solvents, other than tertiary amines, especially ether solvents, are present, preferably they are only present in small amounts, such as at a level of no more than 5% by volume. Typically, when the amine reagent is ammonia, the reaction is generally carried out in the presence of a tertiary amine solvent.

Optionally, the method for the synthesis of a succinimide compound comprises the step of reacting (a) an alkyne in which the two acetylenic carbon atoms are bonded to groups independently selected from hydrogen, optionally substituted alkyl, optionally substituted aryl or aralkyl, or optionally substituted heteroaryl or heteroaralkyl, with (b) carbon monoxide and (c) ammonia or a mono or multifunctional primary amine in which the primary amine group(s) are bonded to an optionally substituted alkyl, optionally substituted aryl or aralkyl, or optionally substituted heteroaryl or heteroaralkyl, in the presence of (d) an iron catalyst and optionally (e) a tertiary amine solvent, wherein the reaction is carried out (i) in bulk amine and/or (ii) either in the absence of ether solvents or if ether solvents are present, the ratio of ether solvents to amines is no more than 1:1. The method for the synthesis of a succinimide compound may, for example, comprise the step of reacting (a) an alkyne other than ethyne, in which the two acetylenic carbon atoms are bonded to groups independently selected from hydrogen, substituted or unsubstituted $C_1$-$C_{12}$ alkyl, substituted or unsubstituted $C_5$-$C_{16}$ aryl or aralkyl, or substituted or unsubstituted $C_5$-$C_{16}$ heteroaryl or heteroaralkyl, with (b) carbon monoxide and (c) ammonia, a monofunctional primary amine or a bifunctional primary amine in which the primary amine group(s) in the mono- or bifunctional primary amine are bonded to substituted or unsubstituted $C_1$-$C_{12}$ alkyl, substituted or unsubstituted $C_5$-$C_{16}$ aryl or aralkyl, or substituted or unsubstituted $C_5$-$C_{16}$ heteroaryl or heteroaralkyl, in the presence of (d) an iron carbonyl catalyst and optionally (e) a tertiary amine solvent, wherein the reaction is carried out (i) in bulk amine and/or (ii) either in the absence of ether solvents or if ether solvents are present, the ratio of ether solvents to amines is no more than 1:1.

The method of the present invention may, for example, produce a succinimide of the formula (I) according to the following scheme:

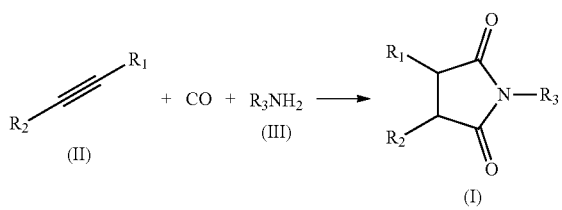

in which alkyne (a) is an alkyne of the formula (II) in which $R_1$ and $R_2$ are each independently selected from hydrogen, optionally substituted alkyl, optionally substituted aryl or aralkyl, and optionally substituted heteroaryl or heteroaralkyl, and amine reagent (c) is an amine of the formula (III) in which $R_3$ is selected from hydrogen, optionally substituted alkyl, optionally substituted aryl or aralkyl, or optionally substituted heteroaryl or heteroaralkyl.

There is no particular restriction on the substituent groups bonded to the two acetylenic carbon atoms on the alkyne starting materials used in the reactions of the present invention, such as the groups $R_1$ and $R_2$ of the alkyne starting material of the formula (II). Examples of suitable substituent groups bonded to the two acetylenic carbon atoms, e.g., examples of suitable groups $R_1$ and $R_2$ substituent groups, include hydrogen, optionally substituted alkyl, optionally substituted aryl or aralkyl, or optionally substituted heteroaryl or heteroaralkyl. Typically, if one of the substituent groups bonded to the two acetylenic carbon atoms is hydrogen the other substituent group is other than hydrogen, i.e., the alkyne is typically other than acetylene (ethyne). Suitable alkyl groups include, straight chain, branched or cyclic alkyl groups, typically having from 1 to 12 carbon atoms, especially from 1 to 8 carbon atoms. The alkyl groups may, optionally, be substituted with one or more substituents, for example, 1, 2, 3 or 4 substituents, such as: fluoro groups; alkoxy, especially $C_1$-$C_8$ alkoxy, including $C_1$-$C_8$ fluoroalkoxy; and amine groups of the formula —NR'R" wherein R' and R" are each independently selected from $C_1$-$C_8$ alkyl or $C_1$-$C_8$ fluoroalkyl. Suitable aryl and aralkyl groups include monocyclic, bicyclic and tricyclic aryl and aralkyl groups typically having from 5 to 16 carbon atoms. The aryl and aralkyl groups may, optionally, be substituted with one or more substituents, for example, 1, 2, 3 or 4 substituents, such as halo groups, especially fluoride; alkyl and fluoroalkyl, especially $C_1$-$C_8$ alkyl and $C_1$-$C_8$ fluoroalkyl; alkoxy and flouroalkoxy, especially $C_1$-$C_8$ alkoxy and $C_1$-$C_8$ fluoroalkoxy; amine groups of the formula —NR'R" wherein R' and R" are each independently selected from $C_1$-$C_8$ alkyl or $C_1$-$C_8$ fluoroalkyl; and further aryl and aralkyl groups, for example, having from 5 to 12 ring atoms and/or from 6 to 16 carbon atoms, such as benzyl. Preferably, substituents on the aralkyl groups are on the aryl, rather than on the alkyl, portion of the aralkyl group. Suitable heteroaryl and heteroaralkyl groups include monocyclic, bicyclic and tricyclic heteroaryl and heteroaralkyl groups typically having from 5 to 16 ring atoms and typically including, from 1 to 5 ring heteroatoms, for example 1, 2 or 3 ring heteroatoms. The ring heteroatoms are each typically selected from oxygen, nitrogen and sulfur. Suitable heteroaryl and heteroaralkyl groups typically include from 4 to 16 carbon atoms. The heteroaryl and heteroaralkyl groups may, optionally, be substituted with one or more substituents, for example, 1, 2, 3 or 4 substituents, such as halo groups, especially fluoride; alkyl and haloalkyl, especially $C_1$-$C_8$ alkyl and $C_1$-$C_8$ fluoroalkyl; alkoxy, especially $C_1$-$C_8$ alkoxy; amine groups of the formula —NR'R" wherein R' and R" are each independently selected from $C_1$-$C_8$ alkyl or $C_1$-$C_8$ fluoroalkyl; and further aryl and aralkyl groups, for example, $C_{5-16}$ aryl and aralkyl groups, such as benzyl. Preferably, substituents on the heteroaralkyl groups are on the heteroaryl, rather than on the alkyl, portion of the heteroaralkyl group.

In one aspect, the substituent groups bonded to the two acetylenic carbon atoms on the alkyne starting materials, e.g., the groups $R_1$ and $R_2$ of the compound of the formula (II), are each independently selected from:
  hydrogen, with the proviso that the substituents are not both simultaneously hydrogen;
  unsubstituted $C_1$-$C_6$ alkyl;
  $C_1$-$C_6$ fluoroalkyl;
  $C_6$-$C_{10}$ mono- or bicyclic aryl or aralkyl optionally substituted on the aryl with one or two substituents selected from unsubstituted $C_1$-$C_6$ alkyl, $C_1$-$C_6$ fluoroalkyl, unsubstituted $C_1$-$C_6$ alkoxy, halo (especially fluoro), phenyl, benzyl, and —NR'R" wherein R' and R" are each independently selected from unsubstituted $C_1$-$C_4$ alkyl; and $C_5$-$C_9$ mono- or bicyclic heteroaryl or heteroaralkyl, optionally substituted on the heteroaryl with one or two substituents selected from unsubstituted $C_1$-$C_6$ alkyl, $C_1$-$C_6$ fluoroalkyl, unsubstituted $C_1$-$C_6$ alkoxy, halo (especially fluoro), phenyl, benzyl, and —NR'R" wherein R' and R" are each independently selected from unsubstituted $C_1$-$C_4$ alkyl, and containing one, two or three ring heteroatoms selected from nitrogen, oxygen and sulfur.

In another aspect, the substituent groups bonded to the two acetylenic carbon atoms on the alkyne starting materials, e.g., the groups $R_1$ and $R_2$ of the compound of the formula (II), are each independently selected from:

hydrogen, with the proviso that the substituents are not both simultaneously hydrogen;

unsubstituted $C_1$-$C_6$ alkyl, especially methyl, ethyl, propyl, butyl, pentyl, hexyl, cyclopentyl and cyclohexyl;

$C_1$-$C_6$ fluoroalkyl, especially trifluoromethyl and trifluoroethyl;

$C_6$-$C_{10}$ mono- or bicyclic aryl, especially phenyl and naphthyl, optionally substituted with one or two substituents selected from unsubstituted $C_1$-$C_6$ alkyl, especially methyl, $C_1$-$C_6$ fluoroalkyl, especially trifluoromethyl, unsubstituted $C_1$-$C_6$ alkoxy, especially methoxy, halo (especially fluoro), benzyl, and —NR'R" wherein R' and R" are each independently selected from unsubstituted $C_1$-$C_4$ alkyl, especially —N(CH$_3$)$_2$; and $C_6$-$C_{10}$ mono- or bicyclic heteroaryl, especially pyridinyl, diazinyl (e.g., pyrimidinyl), indolyl and isoindolyl (e.g., indolyl), and benzothiophene (e.g., 1-benzothiophene), optionally substituted with one or two substituents selected from unsubstituted $C_1$-$C_6$ alkyl, especially methyl, $C_1$-$C_6$ fluoroalkyl (especially trifluoromethyl), unsubstituted $C_1$-$C_6$ alkoxy (especially methoxy), halo (especially fluoro), benzyl, and —NR'R" wherein R' and R" are each independently selected from unsubstituted $C_1$-$C_4$ alkyl, especially —N(CH$_3$)$_2$.

Advantageously, the amine reagent is ammonia or a mono or bifunctional primary amine. In one aspect, the amine reagent is a primary amine, for example, a mono or bifunctional primary amine. The term "monofunctional primary amine" refers to a compound having only one primary amine group and the term "bifunctional primary amine" refers to a compound having two primary amine groups. Suitable mono- or bifunctional primary amine compounds may also have other functional groups in addition to the primary amine groups, such as alkoxy groups, and tertiary amine groups. The skilled person would appreciate that whilst a wide range of additional functional groups can be tolerated in the primary amine compounds used in the method of the invention, the presence of certain functional groups, such as secondary amines and hydroxyls, may interfere with the reaction and so can result in lower yields of desired succinimides products.

There is no particular restriction on the substituent groups present on primary amine that are suitable for use as amine reagents in the reaction of the present invention, such as the substituent $R_3$ in a primary amine reagent of the formula (II). Examples of suitable substituent groups on the primary amines, e.g., examples of suitable $R_3$ groups in addition to hydrogen, include optionally substituted alkyl, optionally substituted aryl or optionally substituted heteroaryl. Suitable alkyl groups include straight chain, branched or cyclic alkyl groups, typically having from 1 to 12 carbon atoms, especially from 1 to 8 carbon atoms. The alkyl groups may, optionally, be substituted with one or more substituents, for example, 1, 2, 3 or 4 substituents, such as halo groups, especially fluoride, chloride or bromide; hydroxy, alkoxy, especially $C_1$-$C_8$ alkoxy, including $C_1$-$C_8$ haloalkoxy; and amine groups of the formula —NR'R" wherein R' and R" are each independently selected from $C_1$-$C_8$ alkyl or $C_1$-$C_8$ haloalkyl, especially fluoroalkyl. Suitable aryl and aralkyl groups include monocyclic, bicyclic and tricyclic aryl and aralkyl groups typically having from 5 to 16 carbon atoms. The aryl and aralkyl groups may, optionally, be substituted with one or more substituents, for example, 1, 2, 3 or 4 substituents, such as halo groups, especially fluoride, chloride or bromide; alkyl and haloalkyl, especially $C_1$-$C_8$ alkyl and $C_1$-$C_8$ haloalkyl, especially fluoroalkyl; alkoxy, especially $C_1$-$C_8$ alkoxy; amine groups of the formula —NR'R" wherein R' and R" are each independently selected from $C_1$-$C_8$ alkyl or $C_1$-$C_8$ fluoroalkyl; and further aryl and aralkyl groups, for example having from 5 to 10 carbon atoms, such as benzyl. Preferably, substituents on the aralkyl groups are on the aryl, rather than on the alkyl, portion of the aralkyl group. Suitable heteroaryl groups include monocyclic, bicyclic and tricyclic heteroaryl and heteroaralkyl groups typically having from 4 to 15 carbon atoms and typically including from 1 to 5 ring heteroatoms, for example 1, 2 or 3 ring heteroatoms. The ring heteroatoms are each typically selected from oxygen, nitrogen and sulfur. The heteroaryl groups may, optionally, be substituted with one or more substituents, for example, 1, 2, 3 or 4 substituents, such as halo groups, especially fluoride; hydroxy; alkyl and fluoroalkyl, especially $C_1$-$C_8$ alkyl and $C_1$-$C_8$ fluoroalkyl; alkoxy, especially $C_1$-$C_8$ alkoxy; amine groups of the formula —NR'R" wherein R' and R" are each independently selected from $C_1$-$C_8$ alkyl; and further aryl and arakyl groups, for example having from 5 to 10 carbon atoms, such as benzyl. Preferably, substituents on the heteroaralkyl groups are on the heteroaryl, rather than on the alkyl, portion of the heteroaralkyl group. Suitable alkyl groups include straight chain, branched or cyclic alkyl groups, typically having from 1 to 12 carbon atoms, especially from 1 to 8 carbon atoms.

In one aspect, the primary amine is selected from a difunctional $C_1$-$C_6$ alkyl amine containing two primary amine groups linked via the alkyl, or a monofunctional primary amine of the formula (III) in which $R_3$ is selected from:

unsubstituted $C_1$-$C_6$ alkyl;

$C_1$-$C_6$ fluoroalkyl;

$C_6$-$C_{10}$ mono- or bicyclic aryl or aralkyl optionally substituted on the aryl with one or two substituents selected from unsubstituted $C_1$-$C_6$ alkyl, $C_1$-$C_6$ fluoroalkyl, unsubstituted $C_1$-$C_6$ alkoxy, halo (especially fluoro), phenyl, benzyl, and —NR'R" wherein R' and R" are each independently selected from unsubstituted $C_1$-$C_4$ alkyl; and $C_5$-$C_9$ mono- or bicyclic heteroaryl or heteroaralkyl, optionally substituted with one or two substituents selected from unsubstituted $C_1$-$C_6$ alkyl, $C_1$-$C_6$ fluoroalkyl, unsubstituted $C_1$-$C_6$ alkoxy, halo, phenyl, benzyl, and —NR'R" wherein R' and R" are each independently selected from unsubstituted $C_1$-$C_4$ alkyl, and containing one, two or three ring heteroatoms selected from nitrogen, oxygen and sulfur.

In another aspect, the primary amine is selected from a difunctional $C_1$-$C_6$ alkyl amine containing two primary amine groups linked via the alkyl, or a monofunctional primary amine of the formula (III) in which $R_3$ is selected from:

unsubstituted $C_1$-$C_6$ alkyl, especially methyl, ethyl, propyl, butyl, pentyl, hexyl, cyclopentyl and cyclohexyl;

$C_1$-$C_6$ fluoroalkyl, especially trifluoromethyl and trifluoroethyl;

$C_6$-$C_{10}$ monocyclic aryl or aralkyl, especially phenyl, naphthyl and benzyl, optionally substituted on the aryl with one or two substituents selected from unsubstituted $C_1$-$C_6$ alkyl, especially methyl, $C_1$-$C_6$ fluoroalkyl, especially trifluoromethyl, unsubstituted $C_1$-$C_6$ alkoxy, especially methoxy, and fluoro; and $C_6$-$C_{10}$ mono- or bicyclic heteroaryl or heteroaralkyl, especially pyridinyl, diazinyl (e.g., pyrimidinyl), indolyl and isoindolyl (e.g., indolyl), optionally substituted on the heteroaryl with one or two substituents selected from unsubstituted $C_1$-$C_6$ alkyl, especially methyl; $C_1$-$C_6$ fluoroalkyl, especially trifluoromethyl; unsubstituted $C_1$-$C_6$ alkoxy, especially methoxy; and fluoro.

The iron catalyst is typically an iron carbonyl catalyst. A preferred iron carbonyl catalyst is $Fe_3(CO)_{12}$. Other suitable iron carbonyl catalysts include $Fe(CO)_5$. The iron catalyst may be used in conjunction with a co-catalyst.

The reaction vessel is typically charged with carbon monoxide to a pressure of at least 240 kPa (20 psig), for example, at least 310 kPa (30 psig), especially at least 380 kPa (40 psig). The reaction vessel is typically charged with carbon monoxide to a pressure of no more than 1140 kPa (150 psig), for example, no more than 790 kPa (100 psig), especially no more than 580 kPa (70 psig).

In the method of the invention, the step of reacting an alkyne, with carbon monoxide and an amine, in the presence of an iron catalyst, is carried out in bulk amine and/or in the present of ether solvents wherein the molar ratio of ether solvents, if present, to amines is no more than 1:1. Whilst the synthesis of succinimides from alkynes and amines in the presence of iron catalyst previously reported by Driller, K. M. et al. (ibid) was in the presence of an ether solvent, such as THF, it has been found that the use of an ether solvent is unnecessary and detrimental to the efficiency of the reaction. It has been found that the reaction proceeds efficiently in bulk amine where no added solvents are present other than excess amine reagents, i.e., a solvent-less reaction, or where the only added solvents are tertiary amines. The term "bulk amine" as used herein refers to the majority of the liquid present in the reactor being amines, such as, for example, constituting 60 wt % or more of the liquid, especially 70% or more of the liquid, for example 80% or more of the liquid.

If ether solvents are present, preferably the molar ratio of ether solvents to amines is no more than 1:1, especially no more than 0.5:1, for example, no more than 0.2:1, such as no more than 0.05:1. The reaction may, for example, be carried out in the absence of substantial amounts of ether solvents, in particular in the absence of substantial amounts of tetrahydrofuran (THF). The term "in the absence of substantial levels of an ether solvent" and the like as used herein refers to ether solvents not being present in the reaction vessel during the reaction step of the method of the invention at levels where it functions as a solvent. Small amounts of ether solvents may be tolerated in the reaction vessel without being materially detrimental to the reaction. Preferably, less than 1 molar ratio of ether solvent compared to the amount of alkyne is present in the reaction vessel during the reaction step of the method of the invention, more preferably less than 0.5 molar ratio of ether solvent to alkyne, especially less than 0.2 molar ratio of ether solvent to alkyne. Advantageously, no more than 10% by volume of the liquid phase of the reaction is ether solvents, such as no more than 5% by volume, especially no more than 1% by volume. Typically no appreciable amounts of ether solvents will be present in the reaction vessel during the reaction step of the method of the invention. For the avoidance of doubt, the alkyne or amine reactants used in the synthesis of succinimides in the method of the present invention may include ether groups and may, for example, include methoxy and other alkoxy substituents. Any such alkyne or amine reactants that include alkoxy groups are not ether solvents, a "solvent" being a fluid used to solvate reactants and or starting materials and which does not take part in the reaction of the present invention. Examples of common ether solvents include tetrahydrofuran (THF), diethyl ether, dibutyl ether, diethyl ether, diethylene glycol diethyl ether, diisopropyl ether, dimethoxyethane, dimethoxymethane, 1,4-dioxane, ethyl butyl ether, methoxyethane, methyl butyl ether, morpholine and tetrahydropyran. Preferably, none of those solvents or other ether solvents are present during the reaction of the invention. It is particularly preferred that the reaction is carried out in the absence of substantial levels of THF.

The reaction may, for example, be carried out in the absence of any solvent, i.e., in the absence of compounds that function to solvate one or more of the starting materials or products and which do not take part in the reaction, including tertiary amines. For example, the reaction may be carried out in the absence of substantial levels of any solvent. Small amounts of solvents may be tolerated in the reaction vessel without being materially detrimental to the reaction. For example, small amounts of toluene may be present. Advantageously, no more than 10% by volume of the liquid phase of the reaction is solvents, such as no more than 5% by volume, especially no more than 1% by volume. Optionally, the ratio of any solvent present to amine reagents is less than 1:1, especially less than 0.5:1, for example less than 0.2:1, such as less than 0.0:1. In one embodiment, the reaction may be carried out in the absence of substantial levels of toluene. Optionally, no more than 10% by volume of the liquid phase of the reaction is toluene, such as no more than 5% by volume, especially no more than 1% by volume. Liquid solvents are typically included in reactions in order to produce a single liquid phase reaction mixture allowing all the reagents to come into contact. When the reaction of the present invention is carried out solvent-free, in the absence of a solvent, one or more of the reagents may be present in non-stoichiometric amounts, and may act as a liquid phase in which the other reagents are suspended or dissolved; however, in such case, no solvents which do not take part in the reaction are present. For example, the reaction may be carried out in excess primary amine, which both acts as a reactant and as the bulk liquid phase.

Alternatively, the reaction may be carried out in the presence of a solvent other than an ether solvent. The reaction may, for example, be carried out in the presence of a tertiary amine, such as triethylamine. Preferably, the reaction is either carried out in the absence of substantial amounts of any solvents, i.e., in the absence of substantial amounts of any added solvents that are not also reagents, or the only solvents present are tertiary amines. Optionally the ratio of any solvent present other than tertiary amines to amine reagents is less than 1:1, especially less than 0.5:1, for example less than 0.2:1, such as less than 0.0:1.

Typically the reaction is carried out at a temperature of at least about 60° C., for example at least about 80° C., especially at least about 100° C. Typically the reaction is carried out at a temperature of no more than about 200° C., for example no more than about 160° C., especially no more than about 140° C. Temperatures in the range of from 90 to 150° C., for example about 120° C. have been found to be particularly suitable for the reaction of the present invention. The reaction temperature is typically the temperature of the liquid phase during the reaction step.

The reaction may be carried out with an excess of amine reagent to alkyne. For example, the reaction may be carried out with at least 2 molar equivalents of amine reagent to alkyne, especially at least 2.5 molar equivalents of amine reagent to alkyne, such as at least a 2.8 molar equivalents of amine reagent to alkyne. When the amine reagent is ammonia, a large excess of ammonia gas is typically used. It has been found that a large excess of amine reagent is not necessary using the method of the present invention in which the reaction is carried out substantially in the absence of an ether solvent. The reaction may be carried out with no more than 10 molar equivalents of amine reagent to alkyne, especially no more than 8 molar equivalents of amine reagent to alkyne, such as no more than 6 molar equivalents of amine reagent to alkyne. The reaction may, for example be carried out with from 2.2 to 5 molar equivalents of primary amine to alkyne, such as, from about 2.8 to about 3.2 molar equivalents of primary amine to alkyne. The reaction may be carried out in the presence of a tertiary amine as a solvent. The reaction may be carried out with approximately stoichiometric amount of ammonia or primary amine reagent, for example, in the presence of a tertiary amine solvent. The reaction may, alternatively, be carried out with excess ammonia or primary amine reagent in the presence of a tertiary amine solvent.

Typically, the reaction time is from about 6 hours to about 48 hours, for example, from about 8 hours to about 36 hours, such as from about 12 to about 36 hours, for example, about 24 hours.

Advantageously, the method of the present invention may be carried out without taking special precautions to exclude moisture or air from the reaction vessel. For example, the reaction of the present invention may be carried out using standard equipment that is reasonably dry which is charged twice with carbon monoxide without having to take special precautions to drive off all moisture from the equipment or the use of argon or other inerting atmospheres. The lack of a need to take special precautions to exclude air is particularly advantageous when the reaction is carried out on a large scale where the practicalities of excluding all air from reaction vessels become onerous.

The Conversion of Succinimides to Quaternary Ammonium Cations

The invention further provides a method of preparing a quaternary ammonium ion comprising the steps of preparing a succinimide compound in accordance with the method described above, and converting the succinimide to a quaternary ammonium ion.

Succinimides may be converted to quaternary ammonium cations for use as structure directing agents by reduction to the corresponding amine followed by alkylation of the nitrogen. For example, the reaction pathway may be:

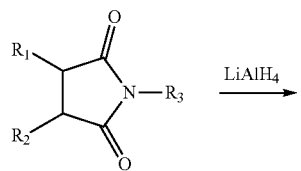

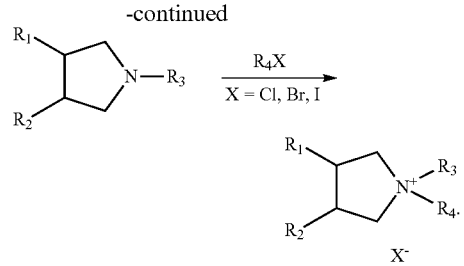

$R_1$, $R_2$ and $R_3$ may be as defined above with reference to the succinimides. $R_4$ may, for example, comprise from 1 to 20 carbon atoms and optionally also include one or more heteroatoms. Optionally, the amine is alkylated with a bifunctional alkylating group, for example, an alkylene group comprising from 1 to 20 carbon atoms and having two leaving groups, for example, substitutable halogen atoms. Such bifunctional alkylating compounds include 1,6-diiodohexane, 1,5-diiodopentane, 1,4-diiodobutane, 1,3-diiodopropane, and their bromo-analogues. Where such a bifunctional alkylating agent is used the quaternary ammonium compound will generally comprise two groups derived from the amine bridged by a bridging group derived from the alkylating agent.

The Synthesis of Molecular Sieves

As mentioned above, the invention provides a process for producing a a molecular sieve, the process comprising the steps of: i) preparing a synthesis mixture capable of forming a molecular sieve, said synthesis mixture comprising a source selected from a source of a tetravalent element Y, a source of a trivalent element X, or a mixture of a source of tetravalent element Y and a source of trivalent element X, and optionally a source of pentavalent element Z, optionally a source of hydroxide ions, optionally a source of halide ions W, and optionally a source of alkali metal ions $M^+$, the synthesis mixture further comprising a structure directing agent Q comprising a cation comprising a pyrrolidinium group in which the ring nitrogen is a quaternary ammonium nitrogen and in which at least one, and preferably both, of the 3- and the 4-positions on the pyrrolidinium ring is substituted with a substituent group other than hydrogen; ii) heating said synthesis mixture under crystallisation conditions for a time of from about 1 to about 100 days to form crystals of said molecular sieve; and iii) recovering said crystals of the molecular sieve from the synthesis mixture.

Optionally, the synthesis mixture contains less than 1 mol % of pentavalent element Z. Optionally, it does not contain any pentavalent element Z. Alternatively, the synthesis mixture contains a pentavalent element Z, for example, the synthesis mixture may contain more than 1 mol % of the pentavalent element Z. The pentavalent element Z may be, for example, phosphorous.

The tetrahedral element Y includes one or more elements selected from the group consisting of Li, Be, Al, P, Si, Ga, Ge, Zn, Cr, Mg, Fe, Co, Ni, Mn, As, In, Sn, Sb, Ti and Zr. Preferably the tetrahedral elements include one or more elements selected from the group consisting of Si, Ge, Sn, Ti and Zr. More preferably, the tetrahedral atoms are Si, Ge or a mixture thereof, even more preferably Si.

Suitable sources of tetravalent element Y depend on the element Y that is selected (e.g., silicon, germanium, strontium, titanium and zirconium). In embodiments where Y is silicon, suitable sources of silicon include silica, colloidal suspensions of silica, precipitated silica alkali metal silicates, tetraalkyl orthosilicates, and fumed silicas. In embodiments where Y is germanium, germanium oxide may be used as a source of germanium.

The trivalent element X is one or more of B, Al, Fe, and Ga, preferably B, Al or a mixture of B and Al. More preferably, the trivalent element is Al.

Suitable sources of trivalent element X depend on the element X that is selected (e.g., boron, aluminum, iron and gallium). In embodiments where X is boron, sources of boron include boric acid, sodium tetraborate and potassium tetraborate. Preferably, the trivalent element X is aluminum, and the aluminum source is aluminum sulfate, aluminum hydroxide, hydrated alumina and mixtures thereof. Other aluminum sources include, but are not limited to, other water-soluble aluminum salts, sodium aluminate, or an aluminum alkoxide, such as aluminum isopropyloxide, or an aluminum metal, such as aluminum in the form of chips.

Alternatively or in addition to previously mentioned sources of elements Y and X, aluminosilicates may also be used as a source of both Y and X elements.

Suitable sources of pentavalent elements Z depend on the element Z that is selected. Preferably, Z is phosphorus. Suitable sources of phosphorous include one or more sources selected from the group consisting of phosphoric acid; organic phosphates, such as triethyl phosphate, tetraethyl-ammonium phosphate, aluminophosphates, and mixtures thereof.

Optionally, the synthesis mixture also contains as source of halide ions W, which may be selected from the group consisting of chloride, bromide or fluoride. The source of halide ions may be any compound capable of releasing halide ions in the molecular sieve synthesis mixture. Non-limiting examples of sources of halide ions include; salts containing one or several halide ions, such as metal halides, preferably where the metal is sodium, potassium, calcium, magnesium, strontium, barium, ammonium or tetraalkylammonium fluorides. If the halide ion is fluoride, a convenient source of halide is HF.

Optionally, the synthesis mixture also contains a source of alkali metal $M^+$. If present, the alkali metal $M^+$ is preferably selected from the group consisting of sodium, potassium and mixtures of sodium and potassium. The sodium source may be sodium hydroxide or sodium aluminate.

The synthesis mixture further comprises a structure directing agent (SDA) Q comprising a cation comprising a pyrrolidinium group in which the ring nitrogen is a quaternary ammonium nitrogen and in which at least one of the 3- and the 4-positions on the pyrrolidinium ring is substituted with a substituent group other than hydrogen Optionally, both the 3- and the 4-positions of the pyrrolidinium group of the SDA Q have a substituent.

Optionally, at least one, and preferably both, of the 3- and 4-positions of the pyrrolidinium ring is substituted with a group comprising from 1 to 20 carbon atoms, and optionally also comprising one or more heteroatoms.

Optionally, the substituents on the 3- and/or 4-positions are independently selected from the group consisting of substituted or unsubstituted alkyl, substituted or unsubstituted aryl, substituted or unsubstituted aralkyl, substituted or unsubstituted heteroaryl and substituted or unsubstituted heteroaralkyl.

Optionally, both the 3- and 4-positions on the pyrrolidinium group are substituted by groups which are independently selected from the group consisting of $C_1$ to $C_{12}$ alkyl, cycloalkyl or alkylaromatic groups.

Optionally, the 3- and 4-positions in the pyrrolidinium group are substituted by groups of identical structure.

Optionally, the 3- and 4-positions on the pyrrolidinium group are substituted by groups independently selected from:
  hydrogen, with the proviso that the substituents are not both simultaneously hydrogen;
  unsubstituted $C_1$-$C_6$ alkyl, especially methyl, ethyl, propyl, butyl, pentyl, hexyl, cyclopentyl and cyclohexyl;
  $C_1$-$C_6$ fluoroalkyl, especially trifluoromethyl and trifluoroethyl;
  $C_6$-$C_{10}$ mono- or bicyclic aryl, especially phenyl and naphthyl, optionally substituted with one or two substituents selected from unsubstituted $C_1$-$C_6$ alkyl, especially methyl, $C_1$-$C_6$ fluoroalkyl, especially trifluoromethyl, unsubstituted $C_1$-$C_6$ alkoxy, especially methoxy, halo (especially fluoro), benzyl, and —NR'R" wherein R' and R" are each independently selected from unsubstituted $C_1$-$C_4$ alkyl, especially —N(CH$_3$)$_2$; and
  $C_6$-$C_{10}$ mono- or bicyclic heteroaryl, especially pyridinyl, diazinyl (e.g., pyrimidinyl), indolyl and isoindolyl (e.g., indolyl), and benzothiophene (e.g., 1-benzothiophene), optionally substituted with one or two substituents selected from unsubstituted $C_1$-$C_6$ alkyl, especially methyl, $C_1$-$C_6$ fluoroalkyl (especially trifluoromethyl), unsubstituted $C_1$-$C_6$ alkoxy (especially methoxy), halo (especially fluoro), benzyl, and —NR'R" wherein R' and R" are each independently selected from unsubstituted $C_1$-$C_4$ alkyl, especially —N(CH$_3$)$_2$.

Optionally, the substituents on the quaternary ammonium nitrogen of the pyrrolidinium group each comprise from 1 to 20 carbon atoms and optionally also include one or more heteroatoms, or the cation comprises two pyrrolidinium groups, the quaternary ammonium nitrogens of each pyrrolidinium group being connected by a bridging group which comprises from 2 to 20 carbon atoms, and optionally includes one or more heteroatoms, and also each having a substituent comprising from 1 to 20 carbon atoms, also optionally including one or more heteroatoms.

Optionally, the substituents on the quaternary ammonium nitrogen of the pyrrolidinium group are independently selected from the group consisting of substituted or unsubstituted alkyl, substituted or unsubstituted aralkyl, and substituted or unsubstituted heteroaralkyl, or the cation comprises two pyrrolidinium groups, the quaternary ammonium nitrogens of each pyrrolidinium group being connected by a bridging group, preferably an alkylene bridging group, and also each having a substituent selected from the group consisting of substituted or unsubstituted alkyl, substituted or unsubstituted aralkyl, and substituted or unsubstituted heteroaralkyl.

Optionally, the substituents on the quaternary ammonium nitrogen of the pyrrolidinium group are each independently selected from the group consisting of $C_1$ to $C_8$ alkyl and cycloalkyl groups or the cation comprises two pyrrolidinium groups, the ring nitrogens of each pryrrolidinium group being connected by a $C_2$ to $C_8$ alkylene group and each of said nitrogens having a further substituent independently selected from the group consisting of $C_1$ to $C_{12}$ alkyl, cycloalkyl or alkylaromatic groups.

Optionally, the structure directing agent Q comprises a cation of formula IV or formula V

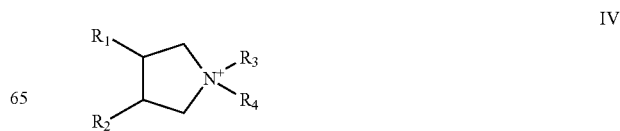

IV

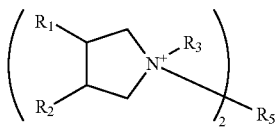

Wherein $R_1$, $R_2$, $R_3$ and $R_4$ are groups containing from 1 to 20 carbon atoms, and optionally, one or more heteroatoms, with the proviso that $R_3$ and $R_4$ do not contain an aromatic or heteroaromatic group directly bonded to the nitrogen of the pyrrolidinium ring; and $R_5$ is a bridging group, preferably comprising from 2 to 20 carbon atoms, optionally, including one or more heteroatoms.

Optionally, $R_1$ and $R_2$ are each independently selected from the group consisting of hydrogen, substituted or unsubstituted alkyl, substituted or unsubstituted aryl, substituted or unsubstituted aralkyl, substituted or unsubstituted heteroaryl and substituted or unsubstituted heteroaralkyl, provided that $R_1$ and $R_2$ cannot both be hydrogen; $R_3$ and $R_4$ are each independently selected from the group consisting of substituted or unsubstituted alkyl, substituted or unsubstituted aralkyl, and substituted or unsubstituted heteroaralkyl; and $R_5$ is a bridging group, preferably a $C_2$ to $C_8$ alkylene group.

Optionally, $R_1$, $R_2$ and $R_3$ are as defined above with respect to the succinimides.

The synthesis may be aided by molecular sieve seeds, with the seeds suitably being present in an amount from about 0.01 ppm by weight to about 10,000 ppm by weight, such as from about 100 ppm by weight to about 5,000 ppm by weight of the synthesis mixture.

Crystallization can be carried out at either static or stirred conditions in a suitable reactor vessel, such as, for example, polypropylene jars or Teflon lined or stainless steel autoclaves, at a temperature of about 100° C. to about 200° C., such as about 150° C. to about 170° C., for a time sufficient for crystallization to occur at the temperature used, e.g., from about 1 day to about 100 days, optionally, from 1 to 50 days, for example, about 2 days to about 20 days. Thereafter, the synthesized crystals are separated from the liquid and recovered.

Optionally, the molecular sieve is a zeolite has a framework type selected from the group consisting of AEI, CHA, STI, FAU, MEL, BEC, MTW and EUO.

Optionally, the molecular sieve is an aluminosilicate or a borosilicate.

The molecular sieve material in its calcined form, may have a chemical composition having the following molar relationship:

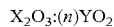

$$X_2O_3:(n)YO_2$$

wherein n is at least about 10, such as about 10 to about 300, X is a trivalent element, such as one or more of B, Al, Fe, and Ga, and Y is a tetravalent element, such as one or more of Si, Ge, Sn, Ti, and Zr. Preferably, X is Al, B or a mixture of Al and B, and Y is Si, Ge or a mixture of Si and Ge. Preferably, X is Al and Y is Si.

In its as-synthesized form, the molecular sieve may have a chemical composition having the following molar relationship:

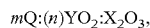

$$mQ:(n)YO_2:X_2O_3,$$

wherein $0.001 < m/n \leq 0.5$, n is at least 10, Q is an organic structure directing agent, X is a trivalent element, such as one or more of B, Al, Fe, and Ga, and Y is a tetravalent element, such as one or more of Si, Ge, Sn, Ti, and Zr. X is Al, B or a mixture of Al and B, and Y is Si, Ge or a mixture of Si and Ge. Preferably, X is Al and Y is Si.

The molecular sieve may alternatively be a crystalline aluminophosphate or silicoaluminophosphate. Those materials may be represented by the formula, on an anhydrous basis:

$$mQ:(Si_xAl_yP_z)O_2$$

where m is the number of moles of Q per mole of $(Si_xAl_yP_z)O_2$ and m has a value from 0.01 to 0.5, preferably from 0.04 to 0.35; x, y, and z respectively represent the mole fraction of Si, Al and P as tetrahedral oxides, and y and z are greater than or equal to 0.01. Preferably, x is greater than 0. Optionally, x is in the range of from greater than 0 to about 0.31, y is in the range of from 0.25 to 1.0, and z is in the range of from 0.25 to 0.9.

To the extent desired and depending on the $X_2O_3/YO_2$ molar ratio of the material, any cations in the as-synthesized molecular sieve can be replaced in accordance with techniques well known in the art by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups 2 to 15 of the Periodic Table of the Elements. As used herein, the numbering scheme for the Periodic Table Groups is as disclosed in Chemical and Engineering News, 63 (5), 27 (1985).

The molecular sieve described herein may be subjected to treatment to remove a portion of or the entire amount of structure directing agent Q used in its synthesis. This is conveniently done by thermal treatment (calcination) in which the as-synthesized material is heated at a temperature of at least about 300° C., preferably at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product, especially in its metal, hydrogen and ammonium forms, is particularly useful in the catalysis of certain organic, e.g., hydrocarbon, conversion reactions.

Use of the Molecular Sieves

The molecular sieve of the present disclosure may be used as an adsorbent or as a catalyst to catalyze a wide variety of organic compound conversion processes including, many of present commercial/industrial importance. Examples of chemical conversion processes which are effectively catalyzed by the crystalline material of this invention, by itself or in combination with one or more other catalytically active substances including other crystalline catalysts, include those requiring a catalyst with acid activity. Examples of organic conversion processes which may be catalyzed by molecular sieves include, cracking, hydrocracking, isomerization, polymerisation, reforming, hydrogenation, dehydrogenation, dewaxing, hydrodewaxing, absorption, alkylation, transalkylation, dealkylation, hydrodecylization, disproportionation, oligomerization, dehydrocyclization and combinations thereof.

The molecular sieve of the present disclosure, when employed either as an adsorbent or as a catalyst should be dehydrated, at least partially. This can be done by heating to a temperature in the range of about 100° C. to about 500° C., such as about 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the molecular sieve in a vacuum, but a longer time is required to obtain a sufficient amount of dehydration.

The molecular sieve described herein may be intimately combined with a hydrogenating component, such as molybdenum, rhenium, nickel, cobalt, chromium, manganese, or a noble metal such as platinum or palladium where a hydrogenation-dehydrogenation function is to be performed. Such component can be in the composition by way of co-crystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

As in the case of many catalysts, it may be desirable to incorporate the molecular sieve with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with molecular sieve, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions.

In addition to the foregoing materials, the molecular sieve can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of molecular sieve and inorganic oxide matrix may vary widely, with the molecular sieve content ranging from about 1 to about 90 percent by weight and more usually, particularly when the composite is prepared in the form of beads, in the range of about 2 to about 80 weight percent of the composite.

EXAMPLES

The following examples illustrate the present invention. Numerous modifications and variations are possible and it is to be understood that within the scope of the appended claims, the invention may be practiced otherwise than as specifically described herein.

Succinimide Examples

The following succinimides of Examples 1 to 7 are illustrative examples of compounds that can be prepared according to the method of the present invention.

| Example | Structure | Name of succinimide |
|---|---|---|
| 1 | 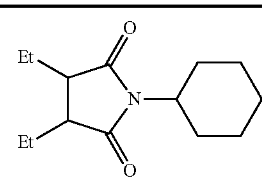 | 1-cyclohexyl-3,4-diethylpyrrolidine-2,5-dione |
| 2 | 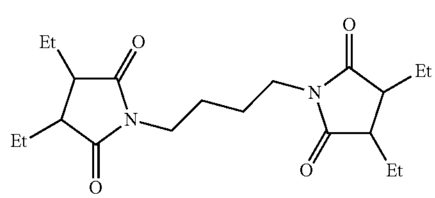 [SMILES: CCC1C(=O)N(CCCCN2C(=O)C(CC)C(CC)C2=O)C(=O)C1CC] | 1,1'-(butane-1,4-diyl)bis(3,4-diethylpyrrolidine-2,5-dione) |
| 3 | 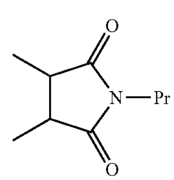 | 3,4-dimethyl-1-propylpyrrolidine-2,5-dione |
| 4 | 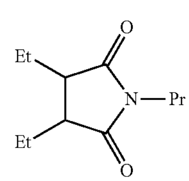 | 3,4-diethyl-1-propylpyrrolidine-2,5-dione |

| Example | Structure | Name of succinimide |
|---|---|---|
| 5 | 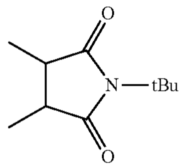 | 1-(tert-butyl)-3,4-dimethylpyrrolidine-2,5-dione |
| 6 | 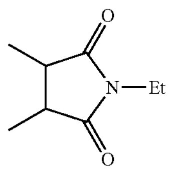 | 1-ethyl-3,4-dimethylpyrrolidine-2,5-dione |
| 7 | 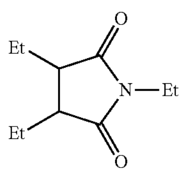 | 1,3,4-triethylpyrrolidine-2,5-dione |

Reagents and Apparatus

The reagents were used as obtained from Aldrich Chemical Company. The triirondodecacarbonyl contained 1-10% methanol according to Aldrich and was used without purification or special handling. Nuclear magnetic resonance (NMR) spectra were obtained using a Bruker Biospin instrument, $^{13}C=100.62$ MHz, $^{1}H=400.13$ MHz. Gas chromatograph mass spectrometry (GCMS)spectra were obtained using Hewlett Packard HP6890GC & HP5973MSD instruments.

General Procedure for Synthesis of Succinimides

The reagents were combined in a 300 mL stainless steel reactor with magnetic stirring. No precautions were taken to exclude air or moisture. Volatile amines were chilled first (for example, to below a temperature where the vapor pressure of the amine is no more than 50 kPa), before opening the bottle and pouring into the reactor. The reactor was sealed, charged with CO to 350 kPA (50 psig), and the pressure released once to de-gas then recharged to 350 kPA (50 psig) with CO. Stirring was begun at 120 RPM and the reactor heated to 120° C. for 24 hr. The reactor was cooled (for example, to below a temperature where the vapor pressure of the liquid phase is no more than 50 kPa), the CO vented, the volatile solvents removed on a rotary evaporator and the product flash distilled in a Kugelrohr distillation apparatus (Aldrich) collecting material boiling from 80-150° C. at 5-20 Pa (0.04-0.15 Torr). For those cases with a significant formamide by-product, 100 g product were dissolved in 200 mL benzene, extracted two times with 50 mL $H_2O$, washed once with 50 mL saturated NaCl, the benzene removed on a rotary evaporator and the product redistilled with a Kugelrohr apparatus.

Example 1

1,3,4-triethylpyrrolidine-2,5-dione

The product was obtained in 82% yield using the general procedure from 3 g $Fe_3(CO)_{12}$ (6.0 mmol), 50 g 3-hexyne (610 mmol), 80 g ethylamine (1780 mmol). The product had the expected $^{13}C$ NMR and $^{1}H$ NMR spectra. $^{1}H$ NMR (CDCl$_3$): δ 3.41(q, 2.4H), 2.30(m, 2.4H), 1.72(m, 2.4), 1.02(t, 4.0H), 0.87(t, 7.4H). $^{13}C$ NMR (CDCl$_3$): δ 179.0 (Cq), 46.1(CH), 33.3(CH$_2$), 24.2(CH$_2$), 12.9(CH$_3$), 10.6 (CH$_3$). GCMS showed a single product with strong molecular ion m/Z=183 and major fragments m/Z=55, 69 84, 126, 140, 155. The same results were obtained in a preparation with 1.5 g Fe$_3$ (CO)$_{12}$ (3.0 mmol), 25 g 3-hexyne (305 mmol), 40 g ethylamine (888 mmol), and 24 g triethylamine (238 mmol).

Example 2

1-ethyl-3,4-dimethylpyrrolidine-2,5-dione

The product was obtained in 75% yield using the general procedure with water extraction to remove N-ethylformamide from 2 g Fe$_3$ (CO)$_{12}$ (4.0 mmol), 25 g 2-butyne (460 mmol), 61.7 g ethylamine (1370 mmol), and 25 g triethylamine (247 mmol). The product was assigned as 85% trans and 15% cis and had the expected $^{13}C$ NMR and $^{1}H$ NMR spectra. $^{1}H$ NMR(CDCl$_3$): δ (major isomer) 3.39(q, 2.0H), 3.2(m, 0.4H), 2.27(m, 1.6H), 1.21(d, 4.8H), 1.03(t, 3.2H). $^{13}C$ NMR (CDCl$_3$): δ (major isomer) 179.1(Cq), 42.8(CH), 33.5(CH$_2$), 14.8(CH$_3$), 12.9(CH$_3$). The assignment of the major isomer as the trans isomer on the assumption that the carbons in the 3,4 position external to the ring will come at higher NMR field (smaller chemical shift) in the cis than in the trans isomer because of greater crowding. The major CH$_3$ ring carbons (trans) in 1-ethyl-3,4-dimethylpyrrolidine-2,5-dione appear at 12.9 ppm and the minor CH$_3$ ring carbons (cis) appear at 11.2 ppm in the $^{13}C$ NMR.

Example 3

1-(tert-butyl)-3,4-dimethylpyrrolidine-2,5-dione

The product was obtained in 95% yield using the general procedure with water extraction to remove N-t-butylformamide from 2 g Fe$_3$ (CO)$_{12}$ (4.0 mmol), 25 g 2-butyne (460 mmol), 100 g t-butylamine (1370 mmol), and 25 g triethylamine (247 mmol). The product was 87% trans and 13% cis. GCMS showed a strong molecular ion m/Z=183 and major fragments 41, 57, 84, 128, 168.

Example 4

3,4-dimethyl-1-propylpyrrolidine-2,5-dione

The product was obtained in 59% yield using the general procedure with water extraction to remove N-n-propylformamide from 7 g $Fe_3(CO)_{12}$ (13.9 mmol), 25 g 2-butyne (460 mmol), 81 g propylamine (1370 mmol), and 25 g triethylamine (247 mmol). The product was 85% trans and 15% cis. It had the expected $^{13}$C NMR and $^1$H NMR spectra. $^1$H NMR ($CDCl_3$): δ 3.36(t, 2.1H), 2.32(m, 1.7H), 1.51(m, 2.3H), 1.26(d, 5.4H), 0.81(d, 3.5H). $^{13}$C NMR ($CDCl_3$): δ 179.5(Cq), 42.9(CH), 40.1($CH_2$), 20.9($CH_2$), 15.1($CH_3$), 11.1($CH_3$). GCMS showed a strong molecular ion m/Z=169 and major fragments 56, 112, 128, 141, 154.

Example 5

3,4-diethyl-1-propylpyrrolidine-2,5-dione

The product was obtained in 74% yield using the general procedure from 1.42 g $Fe_3(CO)_{12}$ (2.82 mmol), 37.5 g 3-hexyne (457 mmol), and 81 g propylamine (1370 mmol). It had the expected $^{13}$C NMR and $^1$H NMR spectra. $^1$H NMR ($CDCl_3$): δ 3.18(m, 1.97H), 2.20(m, 1.89H), 1.59, 1.46, 1.32(m, 6.01H), 0.75(t, 5.97H), 0.61(t, 3.16H). $^{13}$C NMR ($CDCl_3$): δ 178.9(Cq), 45.9(CH), 39.7($CH_2$), 24.0 ($CH_2$), 20.7($CH_2$), 10.9($CH_3$), 10.4($CH_3$). GCMS showed a molecular ion m/Z=197 and major fragments 56, 112, 128, 141, 154.

Example 6

1,1'-(butane-1,4-diyl)bis(3,4-diethylpyrrolidine-2,5-dione)

The product was obtained in 58% yield using the general procedure from 945 mg $Fe_3(CO)_{12}$, (1.88 mmol), 25 g 3-hexyne (304 mmol), 13.4 g 1,4-diaminobutane (152 mmol), and 90 g triethylamine (890 mmol). The product was not characterized by NMR or GCMS, but was converted to 1,4-bis(3,4-diethylpyrrolidin-1-yl)butane by $LiAlH_4$ reduction. Thus, 126.9 g of 1,1'-(butane-1,4-diyl)bis(3,4-diethylpyrrolidine-2,5-dione) (350 mmol) were dissolved in 50 mL anhydrous THF and added to 43.8 g lithium aluminum hydride (1115 mmol) in 1 L anhydrous THF at a rate to maintain gentle reflux. The mixture was stirred and heated at reflux for 48 hr, cooled, and quenched by addition of 110 mL THF+110 mL $H_2O$ followed by 60 g NaOH in 600 mL $H_2O$. The clear supernatant was decanted, the THF removed on a rotary evaporator, the residue extracted with 100 mL 15% NaOH and dried at 80° C. at 2.8 kPa (68 mBar) to constant weight to give 109.8 g (103%) tan oil. Characterization of this derived amine showed that the bis-succinimide had the expected structure. The bis-amine had the expected $^{13}$C NMR and $^1$H NMR spectra. $^1$H NMR ($CDCl_3$): δ 2.51(m, 3.62H), 2.28(m, 2.45H), 2.16, 2.08(m, 5.39H), 1.44, 1.36(m, 12.00H), 1.17(m, 3.94H), 0.74(t, 12.60H). $^{13}$C NMR ($CDCl_3$): δ 60.3($CH_2$), 56.8($CH_2$), 45.9(CH), 28.0($CH_2$), 26.9($CH_2$) and 12.7($CH_3$). GCMS showed it to be greater than 95% pure with molecular ion 308 m/Z and major fragments 55, 84, 126, 140, 154, 182.

Example 7

1-cyclohexyl-3,4-diethylpyrrolidine-2,5-dione

The product was obtained in 91% yield using the general procedure with water extraction to remove N-cyclohexylformamide from 945 mg $Fe_3(CO)_{12}$, (1.88 mmol), 22.5 g 3-hexyne (270 mmol), and 175 g (1770 mmol) cyclohexylamine. Similarly, the product was obtained in 87% yield using the general procedure with water extraction to remove N-cyclohexylformamide from 945 mg $Fe_3(CO)_{12}$, (1.88 mmol), 22.5 g 3-hexyne (270 mmol), 81.3 g (820 mmol) cyclohexylamine and 90 g triethylamine (890 mmol). GCMS showed a weak molecular ion m/Z=237 and major fragments 41, 55, 156.

Further Examples

Further examples of succinimides that can be prepared according to the method of the invention include succinimides 5a to 5n and 5w recited in Tables 1, 2 and 3 of Zhang, J. et al., *Angew. Chem. Int. Ed.* 2010, 49, 6391-6395, by reaction of the amines 1 to 12 and 4a, 4e, 4d, 4s, 4h and 4w disclosed in that document with alkynes in accordance with the general procedure described above. Yet further examples of succinimides that can be prepared according to the method of the invention include succinimides 1 to 15 recited in Tables 2 and 3 of Driller, K. M. et al., *Angew. Chem. Int. Ed.* 2009, 48, 6041-6044 and succinimides 4a to 4t recited in Table 1 of Driller, K. M. et al., *Chem. Eur. J.* 2010, 16, 9606-9615 in which the reaction conditions are altered to those of the present invention.

Quaternary Ammonium Cation Examples

The following quaternary ammonium cations of Examples 8 to 21 are illustrative examples of cations that can be prepared according to the method of the present invention.

| Example | Structure | Name of cation |
|---|---|---|
| 8 | 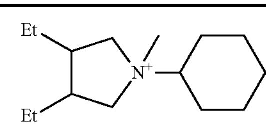 | 1-cyclohexyl-3,4-diethyl-1-methylpyrrolidin-1-ium |
| 9 | 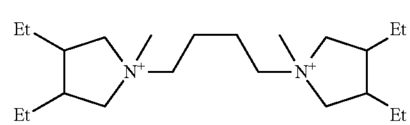 [SMILES: CCC1C[N+](C)(CCCC[N+]2(C)CC(CC)C(CC)C2)CC1CC] | 1,1'-(butane-1,4-diyl)bis(3,4-diethyl-1-methylpyrrolidin-1-ium) |

-continued

| Example | Structure | Name of cation |
|---|---|---|
| 10 | 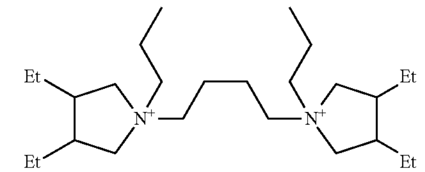 [SMILES: CCC[N+]1(CCCC[N+]2(CCC)CC(CC)C(CC)C2)CC(CC)C(CC)C1] | 1,1'-(butane-1,4-diyl)bis(3,4-diethyl-1-propylpyrrolidin-1-ium) |
| 11 | 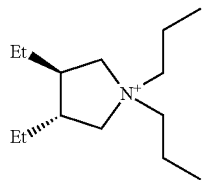 | (3R,4R)-3,4-diethyl-1,1-dipropylpyrrolidin-1-ium + (3S,4S)-3,4-diethyl-1,1-dipropylpyrrolidin-1-ium |
| 12 | 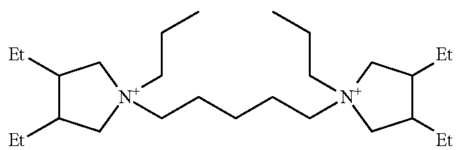 [SMILES: CCC[N+]1(CCCCC[N+]2(CCC)CC(CC)C(CC)C2)CC(CC)C(CC)C1] | 1,1'-(pentane-1,5-diyl)bis(3,4-diethyl-1-propylpyrrolidin-1-ium) |
| 13 | 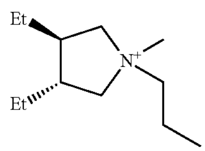 | (3R,4R)-3,4-diethyl-1-methyl-1-propylpyrrolidin-1-ium + (3S,4S)-3,4-diethyl-1-methyl-1-propylpyrrolidin-1-ium |
| 14 | 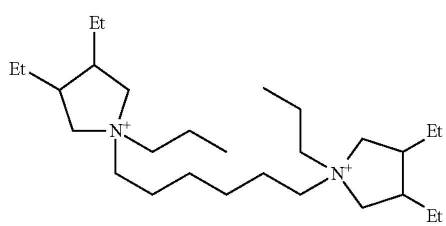 [SMILES: CCC[N+]1(CCCCCC[N+]2(CCC)CC(CC)C(CC)C2)CC(CC)C(CC)C1] | 1,1'-(hexane-1,6-diyl)bis(3,4-diethyl-1-propylpyrrolidin-1-ium |
| 15 | 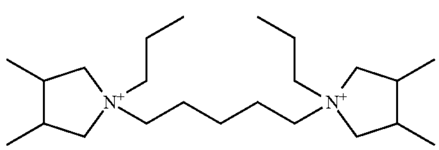 | 1,1'-(pentane-1,5-diyl)bis(3,4-dimethyl-1-propylpyrrolidin-1-ium) |
| 16 | 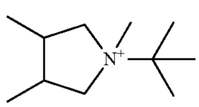 | 1-(tert-butyl)-1,3,4-trimethylpyrrolidin-1-ium |
| 17 | 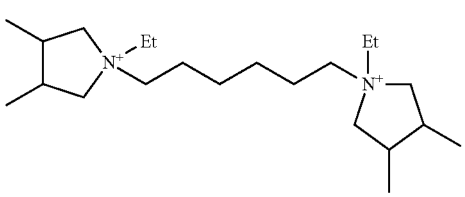 | 1,1'-(hexane-1,6-diyl)bis(1-ethyl-3,4-dimethylpyrrolidin-1-ium) |
| 18 | 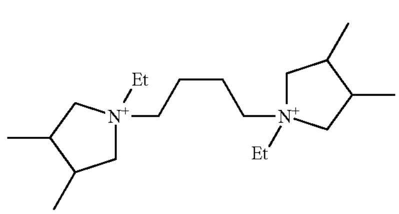 | 1,1'-(butane-1,4-diyl)bis(1-ethyl-3,4-dimethylpyrrolidin-1-ium) |

| Example | Structure | Name of cation |
|---|---|---|
| 19 | 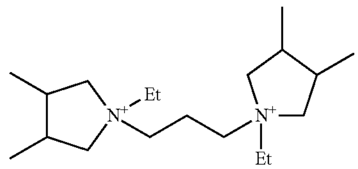 | 1,1'-(propane-1,3-diyl)bis(1-ethyl-3,4-dimethylpyrrolidin-1-ium) |
| 20 | 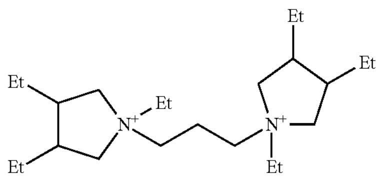 [SMILES: CCC1C[N+](CC)(CCC[N+]2(CC)CC(CC)C(CC)C2)CC1CC] | 1,1'-(propane-1,3-diyl)bis(1,3,4-triethylpyrrolidin-1-ium) |
| 21 | 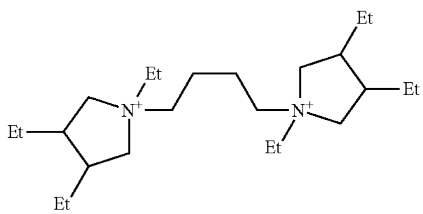 [SMILES: CCC1C[N+](CC)(CCCC[N+]2(CC)CC(CC)C(CC)C2)CC1CC] | 1,1'-(butane-1,4-diyl)bis(1,3,4-triethylpyrrolidin-1-ium) |

General Procedure for Reducing Succinimides to Pyrrolidines

Reduction of the succinimides to pyrrolidines followed the same general procedure in each case. Some variation in the ratio of lithium aluminum hydride to succinimide was tried with the best results at 1.8-2.0 LiAlH4:succinimide. An oven dried, 2 L, 3 neck jacketed flash was assembled hot with Friederich condenser, mechanical stirrer, and equalizing dropping funnel under a strong flow of nitrogen. One liter of anhydrous THF was rapidly poured into the flask followed by the contents of a 25 g bottle of LiAlH4 pellets (Aldrich), typical weight 26.1-27.1 g. A solution of 360 mmol succinimide in 30 mL anhydrous THF was dripped in at a rate to maintain gentle reflux. At the end of the addition, steam was passed through the jacket and reflux continued two days, then chilled water (5° C.) passed through the jacket and the reaction quenched with a mixture of 55 mL $H_2O$+55 mL THF, then the solid converted to a granular white solid by the addition of 36 g NaOH in 360 mL $H_2O$. The solution was decanted from the solid through a small amount of glass wool, the solid extracted with a further 400 mL THF which was decanted and combined with the first decantate. Eighty milliliters of 2M HCl in ether were added and the solvents removed on a rotary evaporator. The resulting aqueous solution was treated with 80 g NaOH in 150 mL $H_2O$. When this had cooled, the upper layer was separated, the lower layer washed with 30 mL ether and the organic layers combined and fractionally distilled from 3 g KOH through a 6" vacuum jacketed Vigreux column.

General Procedure for Alkylation of Pyrrolidines

To a solution of 300 mol amine in acetone (5 to 1 wt to vol) were added 300 meq of the iodo compound. After 2-3 days at room temperature, the solid was filtered, washed well with ether and dried to constant weight at 65° C. Alternatively, for bromo compounds, 300 mmol amine in 150 ml acetonitrile were treated with 285 meq bromo compound. The mixture was heated at reflux for two days, cooled, 150 mL ether added, and the solid filtered, washed well with ether, and dried to constant weight at 65° C.

The halides were then converted to hydroxides using ion exchange resin. The general procedure was as follows: for 181 meq halide, 260 mL Dowex SBR LCNG OH resin (236 meq) were measured with a graduated beaker and the beads transferred to a 1 L plastic bottle using water. The bottle was filled and decanted twice, the solid ammonium halide added followed by enough water to make about 900 mL. The bottle was sealed, rotated slowly for 1-2 hr, the product filtered, and the beads washed with enough water to make about 1.8 L solution. The solution was reduced in volume at 50° C. on a rotary evaporator to a weight such that the concentration was expected to be in the 10-20% range. The concentration was determined by acid/base titration and by integration of the water peak against the organic hydrogens. It was required that the two concentrations agree within 5% of the value obtained.

NMR Referencing $^1H$ and $^{13}C$ NMR spectra are referenced to tetramethylsilane. $^{14}N$ NMR spectra are referenced to the $NH_4^+$ resonance of $NH_4NO_3$ in a 10% solution in $D_2O$.

(3R,4R),(3S,4S)-1-cyclohexyl-3,4-diethylpyrrolidine—Amine A

The product was obtained from the succinimide in 79% yield using the general procedure with a boiling point of 120° C. at 192 mTorr. The product had the expected $^{13}C$ NMR and $^1H$ NMR spectra. $^{13}C$ NMR (CDCl$_3$): δ 63.9(CH), 57.7(CH$_2$), 45.6(CH), 31.7, 28.0, 26.0, 25.2(all CH$_2$), 12.8 (CH$_3$) GCMS showed a single product with strong molecular ion m/Z=209 and major fragments m/Z=55, 108, 166, 180.

1,4-bis(3,4-diethylpyrrolidin-1-yl)butane—Amine B

The product was obtained from the succinimide in 103% yield using the general procedure. The product was obtained as a tan oil which could not be crystallized and which was not purified before use. The product had the expected $^{13}C$ NMR and $^1H$ NMR spectra. $^1H$ NMR (CDCl$_3$): δ 2.51(m, 3.62H), 2.28(m, 2.45H), 2.16, 2.08(m, 5.39H), 1.44, 1.36(m, 12.00H), 1.17(m, 3.94H), 0.74(t, 12.60H). $^{13}C$ NMR (CDCl$_3$): δ 70.1(CH$_2$), 65.1(CH$_2$), 51.3(CH$_2$), 44.1(CH), 43.6(CH), 25.1(CH$_2$), 24.2(CH$_2$), 20.5(CH$_2$), 11.7(CH$_3$). GCMS showed two products with molecular ion m/Z=308 and major fragments m/Z=55, 84, 126, 140, 154, 182.

(3R,4R),(3S,4S)-3,4-diethyl-1-propylpyrrolidine—Amine C

The product was obtained from the succinimide in 89% yield using the general procedure with a boiling point of 200° C. at 760 mTorr. The product had the expected $^{13}$C NMR and $^1$H NMR spectra. $^1$H NMR (CDCl$_3$): δ 2.61(m, 1.88H), 2.33(m, 0.98H), 2.17(m, 2.77H), 1.52-1.14(m, 8.31H), 0.84, 0.82(t, 9.05H). $^{13}$C NMR (CDCl$_3$): d 60.3 (CH$_2$), 58.9(CH$_2$), 46.0(CH), 28.0(CH$_2$), 21.9(CH$_2$), 12.7 (CH$_3$), 11.9(CH$_3$). GCMS showed a single product with molecular ion m/Z=169 and major fragments m/Z=55, 84, 140.

3,4-dimethyl-1-propylpyrrolidine—Amine D

The product was obtained from the succinimide in 66% yield using the general procedure with a boiling point of 145° C. at 180 mTorr. GCMS showed two products in ratio 88:12 (trans and cis) with similar retention times with molecular ion m/Z=141.

1-(tert-butyl)-3,4-dimethylpyrrolidine—Amine E

The product was obtained from the succinimide in 77% yield using the general procedure with a boiling point of 110° C. at 42 mTorr. The product had the expected $^{13}$C NMR spectrum. $^{13}$C NMR (CDCl$_3$): δ 54.7(CH$_2$), 52.6(Cq), 40.7 (CH), 25.7(CH$_3$), 16.8(CH$_3$). $^{13}$C NMR (CDCl$_3$): δ (minor) 53.8(CH$_2$), 52.6(Cq), 34.7(CH), 25.8(CH$_3$), 14.2(CH$_3$). GCMS showed two products in ratio 82:18 (trans and cis) with similar retention times and molecular ion m/Z=155.

1-ethyl-3,4-dimethylpyrrolidine—Amine F

The product was obtained from the succinimide in 81% yield using the general procedure with a boiling point of 137° C. at 760 mTorr. The product had the expected $^{13}$C NMR spectrum. $^{13}$C NMR (CDCl$_3$): δ (major) 61.9(CH$_2$), 50.5(CH$_2$), 40.5(CH), 18.1(CH$_3$), 13.6(CH$_3$). $^{13}$C NMR (CDCl$_3$): δ (minor) 61.9(CH$_2$), 50.5(CH$_2$), 34.2(CH), 18.1 (CH$_3$), 14.2(CH$_3$). $^1$H NMR (CDCl$_3$): δ 2.9-1.54(m, 8.3H), 0.93-0.74(m, 8.7H). GCMS showed two products in ratio 87:13(trans and cis), molecular ion m/Z=127, and major fragments 43, 55, 71, 112, 126.

(3R,4R),(3S,4S)-1,3,4-triethylpyrrolidine—Amine G

The product was obtained from the succinimide in 89% yield using the general procedure with a boiling point of 178° C. at 760 mTorr. The product had the expected $^{13}$C NMR spectrum. $^{13}$C NMR (CDCl$_3$): δ 59.9(CH$_2$), 50.4 (CH$_2$), 46.0(CH), 27.9(CH$_2$), 13.6(CH$_3$), 12.6(CH$_3$). $^1$H NMR (CDCl$_3$): δ 2.56(m, 2.0H), 2.36(m, 1.1H), 2.25(m, 0.96H), 2.12(m, 1.9H), 1.48, 1.38(m, 3.9H), 1.20(m, 2.0H), 0.96(t, 3.1), 0.77(t, 6.1H). GCMS showed a single product with molecular ion 155 and major fragments 43, 55, 71, 96, 140, 154.

Example 8

1-cyclohexyl-3,4-diethyl-1-methylpyrrolidin-1-ium hydroxide

The product was obtained as a 14.9% solution of the hydroxide from the amine A and iodomethane in 62% yield using the general procedure. $^{14}$N NMR (D$_2$O): δ 57.3. $^{13}$C NMR (D$_2$O): δ 75.7(CH), 69.3(CH$_2$), 68.8(CH$_2$), 46.3 (CH$_3$), 43.9(CH), 43.1(CH), 27.4, 26.9, 26.2, 25.0, 25.0, 24.7, 24.4(all CH$_2$), 12.0(CH$_3$), 11.9(CH$_3$).

Example 9

1,1'-(butane-1,4-diyl)bis(3,4-diethyl-1-methylpyrrolidin-1-ium) hydroxide

The product was obtained as a 16.6% solution of the hydroxide from the amine B and iodomethane in 92% yield using the general procedure. $^{14}$N NMR (D$_2$O): δ 54.3 $^{13}$C NMR (D$_2$O): δ 70.1(CH$_2$), 65.1(CH$_2$), 51.3(CH$_3$), 44.1 (CH), 43.6(CH), 25.1(CH$_2$), 24.2(CH$_2$), 20.5(CH$_2$), 11.7 (CH$_3$). $^1$H NMR (D$_2$O): δ 3.83(m, 1.84H), 3.71(m, 2.10H), 3.41(m, 3.94H), 3.24(m, 4.10H), 3.08(s, 6.14H), 2.15(m, 3.55H), 1.86(m, 3.87H), 1.68(m, 3.84H), 1.34(m, 3.95H), 0.85(t, 12.68H).

Example 10

1,1'-(butane-1,4-diyl)bis(3,4-diethyl-1-propylpyrrolidin-1-ium) hydroxide

The product was obtained as a 14.3% solution of the hydroxide from the amine B and iodopropane in 57% yield using the general procedure. The iodide was insoluble in water so the ion exchange was allowed to rotate overnight. $^{14}$N NMR (D$_2$O): δ 55.1 $^{13}$C NMR (D$_2$O): δ (major) 68.7 (CH$_2$), 63.8(CH$_2$), 61.1(CH$_2$), 43.6(CH), 24.2(CH$_2$), 24.1 (CH$_2$), 19.9(CH$_2$), 16.3(CH$_2$), 11.4(CH$_3$), 9.9(CH$_3$). $^{13}$C NMR (D$_2$O): δ (minor) 67.6(CH$_2$), 59.3(CH$_2$), 55.1(CH$_2$), 45.4(CH), 27.3(CH$_2$), 20.9, 20.5, 20.2(CH$_2$), 12.1, 11.7 (CH$_3$). $^1$H NMR (D$_2$O): δ 3.76(m, 3.74H), 3.21(m, 10.95H), 2.07(m, 4.94H), 1.71-1.21(m, 16.4H) 0.92, 0.86(t, 17.9H).

Example 11

(3R,4R), (3S,4S)-3,4-diethyl-1,1-dipropylpyrrolidin-1-ium hydroxide

The product was obtained as a 14.4% solution of the hydroxide from the amine C and iodopropane in 81% yield using the general procedure. $^{14}$N NMR (D$_2$O): δ 59.7 $^{13}$C NMR (D$_2$O): δ 68.3(1:1:1 t)CH$_2$, 63.6(1:1:1 t, CH$_2$), 43.6 (CH), 24.1(CH$_2$), 16.2(CH$_2$), 11.9(CH$_3$), 9.9(CH$_3$). $^1$H NMR (D$_2$O): δ 3.65(m, 2.4H), 3.09(m, 6.3H), 1.95(m, 1.9H), 1.60(m, 5.8H), 1.19(p, 2.0H), 0.82(t, 6.0H), 0.77(t, 5.6H).

Example 12

1,1'-(pentane-1,5-diyl)bis(3,4-diethyl-1-propylpyrrolidin-1-ium) hydroxide

The product was obtained as a 13.1% solution of the hydroxide from the appropriate amine and iodopropane in 81% yield using the general procedure for bromo compounds. $^{14}$N NMR (D$_2$O): δ 55.4 $^{13}$C NMR (D$_2$O): δ 68.6(CH$_2$), 63.4(CH$_2$), 61.9(CH$_2$), 44.1(CH), 43.9(CH), 24.3, 24.2, 22.9, 16.9(CH$_2$), 12.1, 12.1, 10.4(CH$_3$). $^1$H NMR (D$_2$O): δ 4.13(m, 4.0H), 3.66(m, 12.5H), 2.38(m, 3.4H), 2.07(m, 12.5H), 1.92(m, 4.8H), 1.75(m, 4.1H), 1.58(m, 6.7H), 1.04(t, 6.0H), 0.98(2*t, 12.0H).

Example 13

(3R,4R), (3S,4S)-3,4-diethyl-1-methyl-1-propylpyrrolidin-1-ium hydroxide

The product was obtained as a 13.6% solution of the hydroxide from the amine C and iodomethane in 86% yield using the general procedure. The aqueous solution, after filtration and washing the resin, had a small amount of oil. The aqueous solution was extracted once with 400 mL pentane before rotary evaporation. The resulting concentrate was clear. $^{14}$N NMR (D$_2$O): δ 49.3. $^{13}$C NMR (D$_2$O): δ 69.7(CH$_2$), 67.7(CH$_2$), 51.0(CH$_3$), 44.0(CH), 43.5(CH), 25.1(CH$_2$), 24.2(CH$_2$), 16.6(CH$_2$), 11.6(CH$_3$), 11.5(CH$_3$), 9.9(CH$_3$). $^1$H NMR (D$_2$O): δ 3.66(m, 2.0H), 3.13(m, 4.0H), 2.97(s, 3.1H), 2.04(m, 1.9H), 1.65(m, 4.2H), 1.27(m, 1.7H), 0.85(t, 3.1H), 0.79(t, 6.0H).

Example 14

1,1'-(hexane-1,6-diyl)bis(3,4-diethyl-1-propylpyrrolidin-1-ium) hydroxide

The product was obtained as a 19.2% solution of the hydroxide from the amine C and 1,6-diiodohexane in 88% yield using the general procedure but with brief reflux in acetone. $^{14}$N NMR (D$_2$O): δ 55.5. $^{13}$C NMR (D$_2$O): δ 68.4(CH$_2$), 63.6(CH$_2$), 61.8(CH$_2$), 43.5(CH), 25.2(CH$_2$), 24.1(CH$_2$), 22.4(CH$_2$), 16.2(CH$_2$), 11.4(CH$_3$), 9.8(CH$_3$). $^1$H NMR (D$_2$O): δ 3.63(m, 2.2H), 3.09(m, 6.1H), 1.94(m, 1.8H), 1.58(m, 5.8H), 1.25, 1.18(m, 3.8H), 0.77(m, 9.20H).

Example 15

1,1'-(pentane-1,5-diyl)bis(3,4-dimethyl-1-propylpyrrolidin-1-ium) hydroxide

The product was obtained as a 10.3% solution of the hydroxide from the amine D and 1,5-diiodopentane in 65% yield using the general procedure. $^{14}$N NMR (D$_2$O): δ (minor:major=16:84) 57.2, 53.3. $^{13}$C NMR (D$_2$O): δ (major) 70.33(CH$_2$), 64.1(CH$_2$), 62.1(CH$_2$), 38.7(CH$_3$), 22.7(CH$_2$), 16.3(CH$_2$), 16.3(CH$_3$). $^{13}$C NMR (D$_2$O): δ (minor) 69.1 (CH$_2$), 64.1(CH$_2$), 62.1(CH$_2$), 33.0(CH$_2$), 22.4(CH$_2$), 16.2 (CH$_2$), CH$_3$(13.6).

Example 16

1-(tert-butyl)-1,3,4-trimethylpyrrolidin-1-ium hydroxide

The product was obtained as a 13.7% solution of the hydroxide from the amine E and iodomethane in 65% yield using the general procedure. $^{14}$N NMR (D$_2$O): δ (minor:major=17:83) 63.0, 60.5. $^{13}$C NMR (D$_2$O): δ (major) 70.4 (Cq), 67.9(CH$_2$), 66.5(CH$_2$), 49.6(CH$_3$), 40.6(CH), 38.1 (CH), 23.2(CH$_3$), 13.6(CH$_3$), 12.6(CH$_3$). $^{13}$C NMR (D$_2$O): δ (minor) 69.9(Cq), 64.5(CH$_2$), 46.6(CH$_3$), 32.3(CH), 23.6 (CH$_3$), 12.2(CH$_3$).

Example 17

1,1'-(hexane-1,6-diyl)bis(1-ethyl-3,4-dimethylpyrrolidin-1-ium) hydroxide

The product was obtained as a 18.8% solution of the hydroxide from the amine F and 1,6-dibromohexane in 81% yield using the general procedure. $^{14}$N NMR (D$_2$O): δ (minor:major=13:87) 56.9, 54.9. $^{13}$C NMR (D$_2$O): δ (major) 69.6(CH$_2$), 61.8(CH$_2$), 57.8(CH$_2$), 38.8(CH), 25.3(CH$_2$), 22.3(CH$_2$), 13.6(CH$_3$), 8.1(CH$_3$).

Example 18

1,1'-(butane-1,4-diyl)bis(1-ethyl-3,4-dimethylpyrrolidin-1-ium) hydroxide

The product was obtained as a 16.8% solution of the hydroxide from the amine F and 1,4-dibromobutane in 75% yield using the general procedure. $^{14}$N NMR (D$_2$O): δ (minor:major=11:89) 56.8:54.8 $^{13}$C NMR (D$_2$O): δ (major) 69.7(CH$_2$), 61.6(CH$_2$), 58.0(CH$_2$), 38.0(CH), 22.8(CH$_2$), 22.3(CH$_2$), 13.6(CH$_3$), 8.1(CH$_3$).

Example 19

1,1'-(propane-1,3-diyl)bis(1-ethyl-3,4-dimethylpyrrolidin-1-ium) hydroxide

The product was obtained as a 16.8% solution of the hydroxide from the amine F and 1,3-dibromopropane in 82% yield using the general procedure. $^{14}$N NMR (D$_2$O): δ (minor:major=12:88) 56.9:54.9. $^{13}$C NMR (D$_2$O): δ (major) 70.1(CH$_2$), 58.2(CH$_2$), 57.9(CH$_2$), 38.7(CH), 17.7(CH$_2$), 13.5(CH$_3$), 13.2(CH$_3$), 8.0(CH$_3$).

Example 20

1,1'-(propane-1,3-diyl)bis(1,3,4-triethylpyrrolidin-1-ium) hydroxide

The product was obtained as a 15.9% solution of the hydroxide from the amine G and 1,3-dibromopropane in 67% yield using the general procedure. $^{14}$N NMR (D$_2$O): δ 54.7. $^{13}$C NMR (D$_2$O): δ 68.4(CH$_2$), 57.6(CH$_2$), 57.4(CH$_2$), 43.6(CH), 43.5(CH), 24.1(CH$_2$), 23.9(CH$_2$), 17.6(CH$_2$), 11.4(CH$_3$), 11.4(CH$_3$), 8.1(CH$_3$). $^1$H NMR (D$_2$O): δ 3.70(m, 4.1H), 3.23(m, 11.1H), 2.01(b, 6.4H), 1.62(b, 4.1H), 1.22(t, 10.8H), 0.78(t, 11.5H).

Example 21

1,1'-(butane-1,4-diyl)bis(1,3,4-triethylpyrrolidin-1-ium)

The product was obtained as a 19.7% solution of the hydroxide from the amine G and 1,4-dibromobutane in 85% yield using the general procedure. $^{14}$N NMR (D$_2$O): δ 55.0. $^{13}$C NMR (D$_2$O): δ 68.1(CH$_2$), 60.4(CH$_2$), 57.5(CH$_2$), 43.5 (CH), 24.1(CH$_2$), 23.9(CH$_2$), 19.8(CH$_2$), 11.4(CH$_3$), 8.1 (CH$_3$). $^1$H NMR (D$_2$O): δ 3.65(m, 3.7H), 3.23(m, 7.9H), 3.08(m, 4.1H), 1.95(b, 4.3H), 1.62(b, 7.7H), 1.17(m+t, 10.1H), 0.76(12.0H).

Molecular Sieve Synthesis Examples

The following preparations of molecular sieves in Example 22 to 25 are illustrative examples of the methods of molecular sieve synthesis of the present invention.

Example 22

A gel was prepared by combining 329 mL 13.1% 1,1'-(pentane-1,5-diyl)bis(3,4-diethyl-1-propylpyrrolidin-1-ium) hydroxide (1.06 g/mL) as the structure directing agent (SDA), 60.9 mL tetramethoxysilane (1.032 g/mL), 87.5 mL 1% aluminum nitrate (1.006 g/mL), 13.3 mL deionized water, and 19.4 mL 20% hydrofluoric acid (1.06 g/mL) in a 1.5 mL stainless steel vessel. The mixture was stirred until homogeneous. The vessel was placed in a freeze-dry apparatus and the weight reduced by 421 mg. The gel had the following molar ratios:

SDA/Si=0.25,F/Si=0.5,Si/Al=100,H$_2$O/Si=10.

The mixture was stirred until homogeneous and then reacted under autogenous pressure with tumbling at 40 RPM at 150° C. for 10 days in an air oven. The product was separated from the reaction mixture by centrifugation, washed with a substantial amount of deionized water and then subjected to powder X-ray diffraction (XRD). Analysis of the X-ray diffraction pattern showed zeolite designated MEL by the International Zeolite Association.

Example 23

A gel was prepared by combining 8.87 mg germanium oxide, 389 mL 16.6% 1,1'-(butane-1,4-diyl)bis(3,4-diethyl-1-methylpyrrolidin-1-ium) hydroxide (1.018 g/mL) as the structure directing agent (SDA), 91.7 mL tetramethoxysilane, 99.2 mL deionized water, and 33.2 mL 20% hydrofluoric acid in a 1.5 mL stainless steel vessel. The mixture was stirred until homogeneous. The vessel was placed in a freeze-dry apparatus and the weight reduced by 331 mg. The gel had the following molar ratios:

Si/Ge=7,F/Si=0.5,SDA/(Si+Ge)=0.25,H$_2$O/(Si+Ge)=10.

The mixture was stirred until homogeneous and then reacted under autogenous pressure with tumbling at 40 RPM at 150° C. for 10 days in an air oven. The product was separated from the reaction mixture by centrifugation, washed with a substantial amount of deionized water and then subjected to powder X-ray diffraction (XRD). Analysis of the X-ray diffraction pattern showed the product to be the zeolite designated BEC by the International Zeolite Association.

Example 24

A gel was prepared by combining 3.9 mL deionized water, 301 mL 14.3% 1,1'-(butane-1,4-diyl)bis(3,4-diethyl-1-propylpyrrolidin-1-ium) hydroxide as the structure directing agent, 113 mL Ludox LS-30 (30% SiO$_2$), 29.4 mL 10% sodium hydroxide, and 16.0 mL USALCO LSA (8.86% Na$_2$Al$_2$O$_4$ in water) in a 1.5 mL stainless steel vessel. The gel had the following molar ratios.

NaOH/Si=0.15,SDA(OH)$_2$/Si=0.15,Si/Al=40,H$_2$O/Si=33.

The mixture was stirred until homogeneous and then reacted under autogenous pressure without agitation at 160° C. for 4 days in an air oven. The product was separated from the reaction mixture by centrifugation, washed with a substantial amount of deionized water and then subjected to powder X-ray diffraction (XRD). Analysis of the X-ray diffraction pattern showed the product to be the zeolite designated MTW by the International Zeolite Association.

Example 25

A gel was prepared by combining 9.4 mL deionized water, 304 mL 14.9% 1-cyclohexyl-3,4-diethyl-1-methylpyrrolidin-1-ium hydroxide (1.012 g/mL) as structure directing agent (SDA), 103 mL Ludox LS-30 (1.208 g/mL, 30% SiO$_2$), 26.0 mL 17.5% potassium hydroxide (1.16 g/mL), and 27.8 mL 3.47% boric acid, in a 1.5 mL stainless steel vessel. The gel had the following molar ratios:

Si/B=40,SDAOH/Si=0.30,KOH/Si=0.15,H$_2$O/Si=36.

The mixture was stirred until homogeneous and then reacted under autogenous pressure with tumbling at 40 RPM at 120° C. for 28 days in an air oven. The product was separated from the reaction mixture by centrifugation, washed with a substantial amount of deionized water and then subjected to powder X-ray diffraction (XRD). Analysis of the X-ray diffraction pattern showed the product to be the zeolite designated EUO by the International Zeolite Association.

Example 26

A gel with the following composition was prepared:

Si/Al=Si/P=0.15

SDA/(Al+Si+P)=0.47

H$_2$O/(Al+Si+P)=35

SDA=1-tert-butyl-1,3,4-trimethylpyrrolidinium hydroxide.

Cabosperse2017A (17% SiO$_2$) was used as the silica source, Catapal A was used as the alumina source, and phosphoric acid was used as the phosphorus source.

The mixture was stirred until homogeneous and then reacted under autogenous pressure with tumbling at 40 RPM at 160° C. for 4 days in an air oven. The product was separated from the reaction mixture by centrifugation, washed with a substantial amount of deionized water and then subjected to powder X-ray diffraction (XRD). Analysis of the X-ray diffraction pattern showed the product to be zeolite SAPO-34.

It will be appreciated that various presently unforeseen or unanticipated alternatives, modifications, variations or improvements therein may be subsequently made by those skilled in the art, and are also intended to be encompassed by the following claims.

The disclosures of the foregoing publications are hereby incorporated by reference in their entirety. The appropriate components and aspects of the foregoing publications may also be selected for the present materials and methods in embodiments thereof.

We claim:

1. A crystalline molecular sieve, which includes a structure directing agent Q within its pores;
  wherein the structure directing agent Q is a quaternary ammonium ion having a structure and a name selected from the group consisting of:

| Structure | Name of cation |
|---|---|
| (Et-substituted pyrrolidinium with N+ bonded to cyclohexyl) | 1-cyclohexyl-3,4-diethyl-1-methylpyrrolidin-1-ium, |
| (3,4-diethyl pyrrolidinium with two propyl groups on N+) | (3R,4R)-3,4-diethyl-1,1-dipropylpyrrolidin-1-ium + (3S,4S)-3,4-diethyl-1,1-dipropylpyrrolidin-1-ium, |

33
-continued

| Structure | Name of cation |
|---|---|
| (structure) | (3R,4R)-3,4-diethyl-1-methyl-1-propylpyrrolidin-1-ium + (3S,4S)-3,4-diethyl-1-methyl-1-propylpyrrolidin-1-ium, |
| (structure) | 1-(tert-butyl)-1,3,4-trimethylpyrrolidin-1-ium, |
| (structure) | 1,1'-(butane-1,4-diyl)-bis(3,4-diethyl-1-methylpyrrolidin-1-ium), |
| (structure) | 1,1'-(butane-1,4-diyl)-bis(3,4-diethyl-1-propylpyrrolidin-1-ium), |
| (structure) | 1,1'-(pentane-1,5-diyl)-bis(3,4-diethyl-1-propylpyrrolidin-1-ium), |
| (structure) | 1,1'-(hexane-1,6-diyl)-bis(3,4-diethyl-1-propylpyrrolidin-1-ium, |
| (structure) | 1,1'-(pentane-1,5-diyl)-bis(3,4-dimethyl-1-propylpyrrolidin-1-ium), |
| (structure) | 1,1'-(hexane-1,6-diyl)-bis(1-ethyl-3,4-dimethylpyrrolidin-1-ium), |

34
-continued

| Structure | Name of cation |
|---|---|
| (structure) | 1,1'-(butane-1,4-diyl)-bis(1-ethyl-3,4-dimethylpyrrolidin-1-ium), |
| (structure) | 1,1'-(propane-1,3-diyl)-bis(1-ethyl-3,4-dimethylpyrrolidin-1-ium), |
| (structure) | 1,1'-(propane-1,3-diyl)-bis(1,3,4-triethylpyrrolidin-1-ium), and |
| (structure) | 1,1'-(butane-1,4-diyl)-bis(1,3,4-triethylpyrrolidin-1-ium). |

2. A process for producing a crystalline molecular sieve, which includes a structure directing agent Q within its pores; said process comprising the steps of:
  (i) preparing a synthesis mixture capable of forming a molecular sieve, said synthesis mixture comprising a source selected from a source of a tetravalent element Y, a source of a trivalent element X, or a mixture of a source of tetravalent element Y and a source of trivalent element X, and optionally a source of pentavelent element Z, optionally a source of hydroxide ions, optionally a source of halide ions and optionally a source of alkali metal ions $M^+$, the synthesis mixture further comprising a structure directing agent Q;
  (ii) heating said synthesis mixture under crystallization conditions for a time of from about 1 to about 100 days to form crystals of said molecular sieve; and
  (iii) recovering said crystals of said crystalline molecular sieve from said synthesis mixture,
  wherein said structure directing agent Q is a quaternary ammonium ion having a structure and a name selected from the group consisting of:

| Structure | Name of cation |
|---|---|
| (structure) | 1-cyclohexyl-3,4-diethyl-1-methylpyrrolidin-1-ium, |
| (structure) | (3R,4R)-3,4-diethyl-1,1-dipropylpyrrolidin-1-ium + (3S,4S)-3,4-diethyl-1,1-dipropylpyrrolidin-1-ium, |

-continued

| Structure | Name of cation |
|---|---|
| | (3R,4R)-3,4-diethyl-1-methyl-1-propylpyrrolidin-1-ium + (3S,4S)-3,4-diethyl-1-methyl-1-propylpyrrolidin-1-ium, |
| 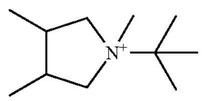 | 1-(tert-butyl)-1,3,4-trimethyl-pyrrolidin-1-ium, |
| 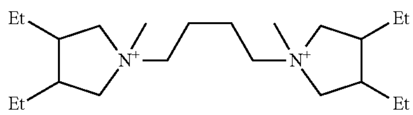 [SMILES: CCC1C[N+](C)(CCCC[N+]2(C)CC(CC)C(CC)C2)CC1CC] | 1,1'-(butane-1,4-diyl)bis(3,4-diethyl-1-methylpyrrolidin-1-ium), |
| 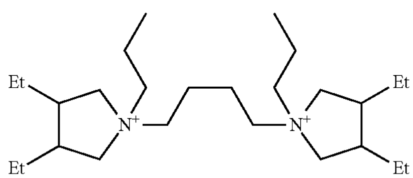 [SMILES: CCC[N+]1(CCCC[N+]2(CCC)CC(CC)C(CC)C2)CC(CC)C(CC)C1] | 1,1'-(butane-1,4-diyl)bis(3,4-diethyl-1-propylpyrrolidin-1-ium), |
| 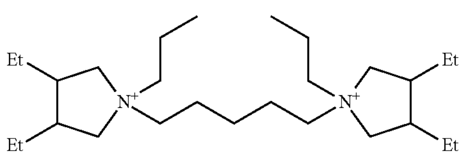 [SMILES: CCC[N+]1(CCCCC[N+]2(CCC)CC(CC)C(CC)C2)CC(CC)C(CC)C1] | 1,1'-(pentane-1,5-diyl)bis(3,4-diethyl-1-propylpyrrolidin-1-ium), |
| 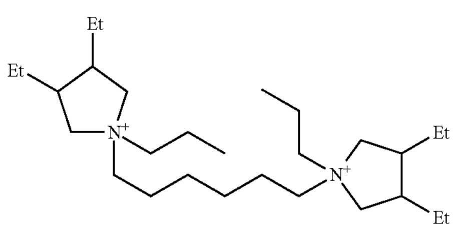 [SMILES: CCC[N+]1(CCCCCC[N+]2(CCC)CC(CC)C(CC)C2)CC(CC)C(CC)C1] | 1,1'-(hexane-1,6-diyl)bis(3,4-diethyl-1-propylpyrrolidin-1-ium, |
| 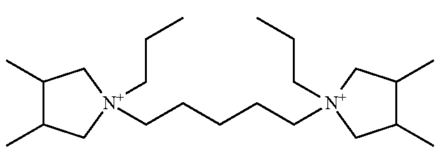 | 1,1'-(pentane-1,5-diyl)bis(3,4-dimethyl-1-propylpyrrolidin-1-ium), |
| 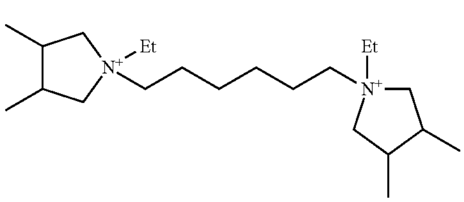 | 1,1'-(hexane-1,6-diyl)bis(1-ethyl-3,4-dimethylpyrrolidin-1-ium), |
| 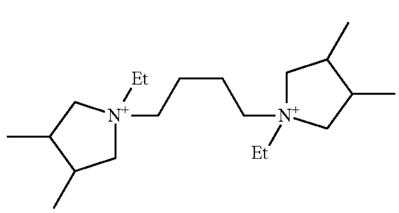 | 1,1'-(butane-1,4-diyl)bis(1-ethyl-3,4-dimethylpyrrolidin-1-ium), |

| Structure | Name of cation |
|---|---|
| 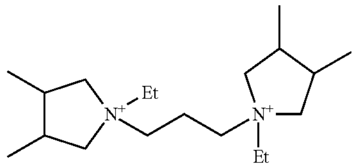 | 1,1'-(propane-1,3-diyl)bis(1-ethyl-3,4-dimethylpyrrolidin-1-ium), |
| 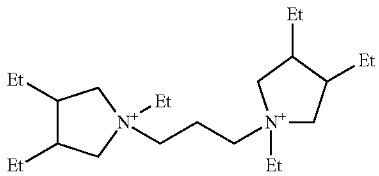 [SMILES: CCC1C[N+](CC)(CCC[N+]2(CC)CC(CC)C(CC)C2)CC1CC] | 1,1'-(propane-1,3-diyl)bis(1,3,4-triethylpyrrolidin-1-ium), and |
| 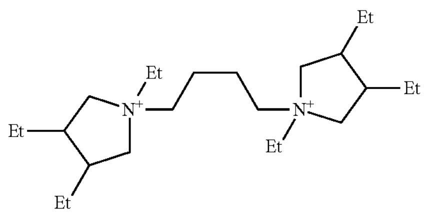 [SMILES: CCC1C[N+](CC)(CCCC[N+]2(CC)CC(CC)C(CC)C2)CC1CC] | 1,1'-(butane-1,4-diyl)bis(1,3,4-triethylpyrrolidin-1-ium). |

3. The process as claimed in claim 2, wherein the synthesis mixture does not contain any pentavelent element Z.

4. The process as claimed in claim 2, wherein said synthesis mixture contains a pentavalent element Z.

5. The process as claimed in claim 3, wherein Y is Si, Ge or a mixture of Si and Ge, and X is Al, B or a mixture of Al and B.

6. The process as claimed in claim 2, wherein said crystalline molecular sieve is an aluminosilicate or a borosilicate.

7. The process as claimed in claim 2, wherein said crystalline molecular sieve is a silicoaluminophosphate (SAPO) or an aluminophosphate (AlPO).

8. The process as claimed in claim 2, wherein said crystalline molecular sieve is a molecular sieve having a framework type selected from the group consisting of AEI, CHA, STI, FAU, MEL, BEC, MTW and EUO.

9. A process for converting a feedstock comprising an organic compound to a conversion product which comprises contacting said feedstock at organic compound conversion compound with a catalyst comprising an active form of the crystalline molecular sieve of claim 1.

* * * * *